＊US011434264B2

(12) United States Patent
Pollock et al.

(10) Patent No.: US 11,434,264 B2
(45) Date of Patent: Sep. 6, 2022

(54) IMMUNOASSAYS FOR DIFFERENTIAL DETECTION OF CLOSTRIDIUM DIFFICILE

(71) Applicants: Quanterix Corporation, Billerica, MA (US); Beth Israel Deaconess Medical Center, Inc., Boston, MA (US)

(72) Inventors: Nira Pollock, Brookline, MA (US); Ciaran Kelly, West Newton, MA (US); David C. Duffy, Arlington, MA (US); Linan Song, Waltham, MA (US); Mingwei Zhao, Wellesley, MA (US)

(73) Assignees: Quanterix Corporation, Billerica, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/550,625

(22) PCT Filed: Feb. 12, 2016

(86) PCT No.: PCT/US2016/017758
§ 371 (c)(1),
(2) Date: Aug. 11, 2017

(87) PCT Pub. No.: WO2016/130923
PCT Pub. Date: Aug. 18, 2016

(65) Prior Publication Data
US 2018/0037614 A1 Feb. 8, 2018

Related U.S. Application Data

(60) Provisional application No. 62/116,073, filed on Feb. 13, 2015.

(51) Int. Cl.
*A61K 39/08* (2006.01)
*C07K 14/33* (2006.01)
*G01N 33/569* (2006.01)
*C07K 16/12* (2006.01)

(52) U.S. Cl.
CPC .......... *C07K 14/33* (2013.01); *C07K 16/1282* (2013.01); *G01N 33/56911* (2013.01); *C07K 2317/33* (2013.01); *G01N 2333/33* (2013.01)

(58) Field of Classification Search
USPC .................................................... 424/139.1
See application file for complete search history.

(56) References Cited

U.S. PATENT DOCUMENTS

| 4,704,692 | A | 11/1987 | Ladner |
| 4,946,778 | A | 8/1990 | Ladner et al. |
| 5,445,934 | A | 8/1995 | Fodor et al. |
| 5,700,637 | A | 12/1997 | Southern |
| 5,807,522 | A | 9/1998 | Brown et al. |
| 6,406,845 | B1 | 6/2002 | Walt et al. |
| 6,482,593 | B2 | 11/2002 | Walt et al. |
| 6,599,331 | B2 | 7/2003 | Chandler et al. |
| 7,214,640 | B2 | 5/2007 | Margetts |
| 8,343,726 | B2 | 1/2013 | Boone et al. |
| 2003/0143555 | A1 | 7/2003 | Bourget et al. |
| 2007/0259381 | A1 | 11/2007 | Rissin et al. |
| 2007/0259385 | A1 | 11/2007 | Rissin et al. |
| 2007/0259448 | A1 | 11/2007 | Rissin et al. |
| 2009/0283407 | A1 | 11/2009 | Shah et al. |
| 2010/0047773 | A1 | 2/2010 | Koch et al. |
| 2010/0075355 | A1 | 3/2010 | Duffy et al. |
| 2010/0075407 | A1 | 3/2010 | Duffy et al. |
| 2010/0075439 | A1 | 3/2010 | Duffy et al. |
| 2010/0075862 | A1 | 3/2010 | Duffy et al. |
| 2010/0233734 | A1 | 9/2010 | Hobbs |
| 2011/0212462 | A1 | 9/2011 | Duffy et al. |
| 2011/0212537 | A1 | 9/2011 | Rissin et al. |
| 2011/0212848 | A1 | 9/2011 | Duffy et al. |
| 2011/0223585 | A1 | 9/2011 | Gullberg et al. |
| 2011/0245097 | A1 | 10/2011 | Rissin et al. |
| 2012/0196774 | A1 | 8/2012 | Fournier et al. |
| 2012/0326104 | A1 | 12/2012 | Kwon et al. |
| 2013/0288249 | A1 | 10/2013 | Gullberg et al. |
| 2013/0330371 | A1* | 12/2013 | Anderson ............... C07K 14/33 424/190.1 |
| 2014/0038184 | A1 | 2/2014 | Jin et al. |
| 2014/0194311 | A1 | 7/2014 | Gullberg et al. |
| 2015/0141272 | A1* | 5/2015 | Gordon ................ C12Q 1/6804 506/9 |
| 2016/0376642 | A1 | 12/2016 | Landegren et al. |

FOREIGN PATENT DOCUMENTS

| CA | 2768528 A1 * | 2/2011 | ............ C07K 14/33 |
| CA | 2768528 A1 | 2/2011 | |
| WO | WO 87/04462 A1 | 7/1987 | |

(Continued)

OTHER PUBLICATIONS

Chang et al. Journal of Immunological Methods vol. 378, No. 1-2, pp. 1-28, 2012 (Year: 2012).*
Rissin et al. Nature Technology vol. 28, No. 6, Jun. 2010 (Year: 3010).*
[No Author Listed], C. Diff Quik Chek Complete. Alere North America, LLC. Apr. 2016:16 pages.
[No Author Listed], C. difficile Tox A/B II Package Insert. TechLab, Inc. Mar. 2008:32 pages.
[No Author Listed], GeneXpert C. difficile package insert. Cepheid, Inc. May 2012:14 pages.
[No Author Listed], Illumigene C. difficile package insert. Meridian Bioscience, Inc. Revised Aug. 2013:16 pages.
[No Author Listed], ImmunoCard Toxins A & B. Meridian Bioscience, Inc. Apr. 2009:13 pages.

(Continued)

*Primary Examiner* — Jana A Hines
*Assistant Examiner* — Khatol S Shahnan Shah
(74) *Attorney, Agent, or Firm* — Wolf, Greenfield & Sacks, P.C.

(57) ABSTRACT

Ultrasensitive and quantitative assays for detecting toxins of *Clostridium difficile*, which may involve digital ELISA, are provided. Also provided herein are differential detection assays that allow for distinguishing toxin B of highly virulent *Clostridium difficile* strains from toxin B of less virulent strains.

30 Claims, 9 Drawing Sheets

(56) References Cited

FOREIGN PATENT DOCUMENTS

| WO | 95/35505 A1 | 12/1995 |
|---|---|---|
| WO | 98/50782 A2 | 11/1998 |
| WO | 2005/095262 A1 | 10/2005 |
| WO | WO 2009/029073 A1 | 3/2009 |
| WO | WO 2010/039179 A1 | 4/2010 |
| WO | WO 2011/109364 A2 | 9/2011 |
| WO | WO 2011/109372 A1 | 9/2011 |
| WO | WO 2011/109379 A1 | 9/2011 |

OTHER PUBLICATIONS

[No Author Listed], Premier Toxins A & B Package Insert. Meridian Bioscience, Inc. Apr. 2009:15 pages.
[No Author Listed], VIDAS C. difficile Toxin A & B package insert. BioMerieux. May 2011:12 pages.
Akerlund et al., Correlation of disease severity with fecal toxin levels in patients with Clostridium difficile-associated diarrhea and distribution of PCR ribotypes and toxin yields in vitro of corresponding isolates. J Clin Microbiol. Feb. 2006;44(2):353-8.
Antunes et al., Molecular methods to study transcriptional regulation of Clostridium difficile toxin genes. Methods Mol Biol. 2010;646:93-115. doi: 10.1007/978-1-60327-365-7_7.
Baker et al., Clinical relevance of a positive molecular test in the diagnosis of Clostridium difficile infection. J Hosp Infect. Aug. 2013;84(4):311-5. doi: 10.1016/j.jhin.2013.05.006. Epub Jul. 5, 2013.
Buck et al., Monoclonal antibodies specific for cell culture mycoplasmas. In Vitro. Apr. 1982;18(4):377-81.
Burnham et al., Diagnosis of Clostridium difficile infection: an ongoing conundrum for clinicians and for clinical laboratories. Clin Microbiol Rev. Jul. 2013;26(3):604-30. Review.
Clabots et al., Development of a rapid and efficient restriction endonuclease analysis typing system for Clostridium difficile and correlation with other typing systems. J Clin Microbiol. Jul. 1993;31(7):1870-5.
Cloud et al., Clostridium difficile strain NAP-1 is not associated with severe disease in a nonepidemic setting. Clin Gastroenterol Hepatol. Aug. 2009;7(8):868-873.e2. doi: 10.1016/j.cgh.2009.05.018. Epub May 22, 2009.
Cohen et al., Clinical Practice Guidelines for Clostridium difficile Infection in Adults: 2010 Update by the Society for Healthcare Epidemiology of America (SHEA) and the Infectious Diseases Society of America (IDSA). Infection Control & Hospital Epidemiology. May 2010;31(5):431-55. Epub Jan. 2, 2010.
Crobach et al., European Society of Clinical Microbiology and Infectious Diseases (ESCMID): data review and recommendations for diagnosing Clostridium difficile-infection (CDI). Clin Microbiol Infect. Dec. 2009;15(12):1053-66. doi: 10.1111/j.1469-0691.2009.03098.x. Review.
Deshpande et al., Diagnostic accuracy of real-time polymerase chain reaction in detection of Clostridium difficile in the stool samples of patients with suspected Clostridium difficile Infection: a meta-analysis. Clin Infect Dis. Oct. 2011;53(7):e81-90. doi: 10.1093/cid/cir505.
Eastwood et al., Comparison of nine commercially available Clostridium difficile toxin detection assays, a real-time PCR assay for C. difficile tcdB, and a glutamate dehydrogenase detection assay to cytotoxin testing and cytotoxigenic culture methods. J Clin Microbiol. Oct. 2009;47(10):3211-7. doi: 10.1128/JCM.01082-09. Epub Aug. 26, 2009.
Freeman et al., The changing epidemiology of Clostridium difficile infections. Clin Microbiol Rev. Jul. 2010;23(3):529-49. doi: 10.1128/CMR.00082-09. Review.
Goorhuis et al., Emergence of Clostridium difficile infection due to a new hypervirulent strain, polymerase chain reaction ribotype 078. Clin Infect Dis. Nov. 1, 2008;47(9):1162-70. doi: 10.1086/592257.

He et al., An ultrasensitive rapid immunocytotoxicity assay for detecting Clostridium difficile toxins. J. Microbiol Methods. Jul. 2009;78(1):97-100.
Johnson et al., Fatal pseudomembranous colitis associated with a variant Clostridium difficile strain not detected by toxin A immunoassay. Ann Intern Med. Sep. 18, 2001;135(6):434-8.
Kader et al., Single toxin detection is inadequate to diagnose Clostridium difficile diarrhea in pediatric patients. Gastroenterology. Dec. 1998;115(6):1329-34.
Kamboj et al., Relapse versus reinfection: surveillance of Clostridium difficile infection. Clin Infect Dis. Nov. 2011;53(10):1003-6. doi: 10.1093/cid/cir643. Epub Oct. 5, 2011.
Kan et al., Isolation and detection of single molecules on paramagnetic beads using sequential fluid flows in microfabricated polymer array assemblies. Lab Chip. Mar. 7, 2012;12(5):977-85. doi: 10.1039/c2lc20744c. Epub Dec. 16, 2011.
Karlsson et al., Induction of toxins in Clostridium difficile is associated with dramatic changes of its metabolism. Microbiology. Nov. 2008;154(Pt 11):3430-6. doi: 10.1099/mic.0.2008/019778-0.
Kawasar, Effective utilization of evolving methods for the laboratory diagnosis of Clostridium difficile infection. Clin Infect Dis. Nov. 2011;53(9):964. doi: 10.1093/cid/cir614. Epub Sep. 29, 2011.
Kelly et al., Anti-Clostridium difficile bovine immunoglobulin concentrate inhibits cytotoxicity and enterotoxicity of C. difficile toxins. Antimicrob Agents Chemother. Feb. 1996;40(2):373-9.
Kohler et al., Continuous cultures of fused cells secreting antibody of predefined specificity. Nature. Aug. 7, 1975;256(5517):495-7.
Koo et al., Real-time polymerase chain reaction detection of asymptomatic Clostridium difficile colonization and rising C. difficile-associated disease rates. Infect Control Hosp Epidemiol. Jun. 2014;35(6):667-73. doi: 10.1086/676433. Epub Apr. 22, 2014.
Kuehne et al., The role of toxin A and toxin B in Clostridium difficile infection. Nature. Oct. 7, 2010;467(7316):711-3. doi: 10.1038/nature09397. Epub Sep. 15, 2010.
Kyne et al., Asymptomatic carriage of Clostridium difficile and serum levels of IgG antibody against toxin A. N Engl J Med. Feb. 10, 2000;342(6):390-7.
Leibowitz et al., Similar Proportions of Stool Specimens From Hospitalized Children With and Without Diarrhea Test Positive for Clostridium difficile. The Pediatric Infectious Disease Journal. Mar. 2015;34(3):261-6.
Lepor et al., Clinical evaluation of a novel method for the measurement of prostate-specific antigen, AccuPSA(TM), as a predictor of 5-year biochemical recurrence-free survival after radical prostatectomy: results of a pilot study. BJU Int. Jun. 2012;109(12):1770-5. doi: 10.1111/j.1464-410X.2011.10568.x. Epub Oct. 12, 2011.
Lim et al., Emergence of a ribotype 244 strain of Clostridium difficile associated with severe disease and related to the epidemic ribotype 027 strain. Clin Infect Dis. Jun. 2014;58(12):1723-30. doi: 10.1093/cid/ciu203. Epub Apr. 4, 2014.
Limaey et al., Pseudomembranous colitis caused by a toxin A(−) B(+) strain of lostridium difficile. J Clin Microbiol. Apr. 2000;38(4):1696-7.
Loo et al., A Predominantly Clonal Multi-Institutional Outbreak of Clostridium difficile-Associated Diarrhea with High Morbidity and Mortality. N. Engl. J. Med. Dec. 2005;353:2442-9.
Louie et al., Clinical Study Group. Fidaxomicin versus vancomycin for Clostridium difficile infection. N Engl J Med. Feb. 3, 2011;364(5):422-31. doi: 10.1056/NEJMoa0910812.
Lyras et al., Toxin B is essential for virulence of Clostridium difficile. Nature. Apr. 30, 2009;458(7242):1176-9. doi: 10.1038/nature07822. Epub Mar. 1, 2009.
Magill et al., Emerging Infections Program Healthcare-Associated Infections and Antimicrobial Use Prevalence Survey Team. Multistate point-prevalence survey of health care-associated infections. N Engl J Med. Mar. 27, 2014;370(13):1198-208. doi: 10.1056/NEJMoa1306801.
McDonald et al., An epidemic, toxin gene-variant strain of Clostridium difficile. N Engl J Med. Dec. 8, 2005;353(23):2433-41. Epub Dec. 1, 2005.
McFarland et al., Nosocomial acquisition of Clostridium difficile infection. N Engl J Med. Jan. 26, 1989;320(4):204-10.

(56) References Cited

OTHER PUBLICATIONS

McFarland et al., Pediatric Clostridium difficile: a phantom menace or clinical reality? J Pediatr Gastroenterol Nutr. Sep. 2000;31(3):220-31. Review.
Ota et al., Clostridium difficile Testing Algorithms Using Glutamate Dehydrogenase Antigen and C. difficile Toxin Enzyme Immunoassays with C. difficile Nucleic Acid Amplification Testing Increase Diagnostic Yield in a Tertiary Pediatric Population. J. Clin. Microbiol. 2012;50(4): 1185-8.
Petrella et al., Decreased cure and increased recurrence rates for Clostridium difficile infection caused by the epidemic C. difficile BI strain. Clin Infect Dis. Aug. 2012;55(3):351-7. doi: 10.1093/cid/cis430. Epub Apr. 20, 2012.
Planche et al., Differences in outcome according to Clostridium difficile testing method: a prospective multicentre diagnostic validation study of C difficile infection. Lancet Infect Dis. Nov. 2013;13(11):936-45. doi: 10.1016/81473-3099(13)70200-7. Epub Sep. 3, 2013.
Polage et al., Outcomes in patients tested for Clostridium difficile toxins. Diagn Microbiol Infect Dis. Dec. 2012;74(4):369-73. doi: 10.1016/j.diagmicrobio.2012.08.019. Epub Sep. 23, 2012.
Riegler et al., Clostridium difficile toxin B is more potent than toxin A in damaging human colonic epithelium in vitro. J Clin Invest. May 1995;95(5):2004-11.
Rissin et al., Simultaneous detection of single molecules and singulated ensembles of molecules enables immunoassays with broad dynamic range. Anal Chem. Mar. 15, 2011;83(6):2279-85. doi: 10.1021/ac103161b. Epub Feb. 23, 2011.
Rissin et al., Single-molecule enzyme-linked immunosorbent assay detects serum proteins at subfemtomolar concentrations. Nat Biotechnol. Jun. 2010;28(6):595-9. doi: 10.1038/nbt.1641. Epub May 23, 2010. Supporting Information Included.
Rousseau et al., Prevalence and diversity of Clostridium difficile strains in infants. J Med Microbiol. Aug. 2011;60(Pt 8):1112-8. doi: 10.1099/jmm.0.029736-0. Epub Mar. 10, 2011.
Rupnik et al., Clostridium difficile infection: new developments in epidemiology and pathogenesis. Nat Rev Microbiol. Jul. 2009;7(7):526-36. doi: 10.1038/nrmicro2164. Review.
Rupnik, Heterogeneity of large clostridial toxins: importance of Clostridium difficile toxinotypes. FEMS Microbiol Rev. May 2008;32(3):541-55. doi: 10.1111/j.1574-6976.2008.00110.x. Epub Apr. 3, 2008. Review.
Ryder et al., Assessment of Clostridium difficile infections by quantitative detection of tcdB toxin by use of a real-time cell analysis system. J Clin Microbiol. Nov. 2010;48(11):4129-34. doi: 10.1128/JCM.01104-10. Epub Aug. 18, 2010.
Schutze et al., Committee on Infectious Diseases; American Academy of Pediatrics. Clostridium difficile infection in infants and children. Pediatrics. Jan. 2013;131(1):196-200. doi: 10.1542/peds. 2012-2992. Epub Dec. 31, 2012. Review.
Selvaraju et al., Detection of toxigenic Clostridium difficile in pediatric stool samples: an evaluation of Quik Check Complete Antigen assay, BD GeneOhm Cdiff PCR, and ProGastro Cd PCR assays. Diagn Microbiol Infect Dis. Nov. 2011;71(3):224-9. doi: 10.1016/j.diagmicrobio.2011.07.015. Epub Sep. 6, 2011.
Song et al., Single molecule measurements of tumor necrosis factor α and interleukin-6 in the plasma of patients with Crohn's disease. J Immunol Methods. Sep. 30, 2011;372(1-2):177-86. doi: 10.1016/j.jim.2011.07.015. Epub Jul. 27, 2011.
Tenover et al., Comparison of strain typing results for Clostridium difficile isolates from North America. J Clin Microbiol. May 2011;49(5):1831-7. doi: 10.1128/JCM.02446-10. Epub Mar. 9, 2011.
Tenover et al., Impact of strain type on detection of toxigenic Clostridium difficile: comparison of molecular diagnostic and enzyme immunoassay approaches. J Clin Microbiol. Oct. 2010;48(10):3719-24. doi: 10.1128/JCM.00427-10. Epub Aug. 11, 2010.
Tenover et al., Laboratory Diagnosis of Clostridium difficile Infection. The Journal of Molecular Diagnostics. Nov. 2011;13(6):573-82.
Warny et al., Toxin production by an emerging strain of Clostridium difficile associated with outbreaks of severe disease in North America and Europe. The Lancet. Sep. 2005;366(9491):1079-84. Epub Sep. 22, 2005.
Wilcox et al., What is the current role of algorithmic approaches for diagnosis of Clostridium difficile infection? J Clin Microbiol. Dec. 2010;48(12):4347-53. doi: 10.1128/JCM.02028-10. Epub Oct. 27, 2010.
Wilson et al., Fifth-generation digital immunoassay for prostate-specific antigen by single molecule array technology. Clin Chem. Dec. 2011;57(12):1712-21. doi: 10.1373/clinchem.2011.169540. Epub Oct. 13, 2011.
Zetterberg et al., Hypoxia due to cardiac arrest induces a time-dependent increase in serum amyloid β levels in humans. PLoS One. 2011;6(12):e28263. doi: 10.1371/journal.pone.0028263. Epub Dec. 14, 2011. 6 pages.
Kelly et al., Clostridium difficile—More Difficult Than Ever. The New England Journal of Medicine. Oct. 2008;359(18):1932-40 with erratum. Review.
Kraft et al., A Laboratory Medicine Best Practices Systematic Review and Meta-analysis of Nucleic Acid Amplification Tests (NAATs) and Algorithms Including NAATs for the Diagnosis of Clostridioides (Clostridium) difficile in Adults. Clinical Microbiology Best Practices. Jul. 2019;32(3):34 pages.
Pollock, Ultrasensitive Detection and Quantification of Toxins for Optimized Diagnosis of Clostridium difficile Infection. Journal of Clinical Microbiology. Feb. 2016;54(2):259-64.
Sharp et al., A Practical Guidance Document for the Laboratory Detection of Toxigenic Clostridium difficile. American Society for Microbiology. Sep. 21, 2010:3 pages.
Chang et al., Single molecule enzyme-linked immunosorbent assays: theoretical considerations. J Immunol Methods. Apr. 30, 2012;378(1-2):102-15. doi: 10.1016/j.jim.2012.02.011. Epub Feb. 20, 2012.
Nguyen et al., Enzyme immunoassay (ELISA) for detection of Clostridium difficile toxin B in specimens of faeces. J Med Microbiol. Apr. 1990;31(4):251-7.
Rissin et al., Multiplexed single molecule immunoassays. Lab Chip. Aug. 7, 2013;13(15):2902-11.
Wilson et al., The Simoa HD-1 Analyzer: A Novel Fully Automated Digital Immunoassay Analyzer with Single-Molecule Sensitivity and Multiplexing. J Lab Autom. Aug. 2016;21(4):533-47. Epub Jun. 15, 2015.
Asanov et al., A platform for combined DNA and protein microarrays based on total internal reflection fluorescence. Sensors (Basel). 2012;12(2):1800-15. doi: 10.3390/s120201800. Epub Feb. 9, 2012.
Giraud et al., Fluorescence lifetime biosensing with DNA microarrays and a CMOS-SPAD imager. Biomed Opt Express. Nov. 4, 2010;1(5):1302-1308. doi: 10.1364/BOE.1.001302.
Kan et al., Isolation and detection of single molecules on paramagnetic beads using sequential fluid flows in microfabricated polymer array assemblies. Lab Chip. Mar. 7, 2012;12(5):977-85. Epub Dec. 16, 2011.
Kokalj et al., Building bio-assays with magnetic particles on a digital microfluidic platform. N Biotechnol. Sep. 25, 2015;32(5):485-503. doi: 10.1016/j.nbt.2015.03.007. Epub Mar. 23, 2015.
Konry et al., Microsphere-based rolling circle amplification microarray for the detection of DNA and proteins in a single assay. Anal Chem. Jul. 15, 2009;81(14):5777-82. doi: 10.1021/ac900694y.
Li et al., Typing of multiple single-nucleotide polymorphisms by a microsphere-based rolling circle amplification assay. Anal Chem. Dec. 1, 2007;79(23):9030-8. doi: 10.1021/ac701702t. Epub Nov. 1, 2007.
Ma et al., Multiplex detection of histone-modifying enzymes by total internal reflection fluorescence-based single-molecule detection. Chem Commun (Camb). Jan. 21, 2016;52(6):1218-21. doi: 10.1039/c5cc08797j. Abstract only.
Mullenix et al., Rolling Circle Amplification Improves Sensitivity in Multiplex Immunoassays on Microspheres. Clin Chem. Oct. 1, 2002;48(10):1855-8. doi: 10.1093/clinchem/48.10.1855.
Philippova et al., Magnetic polymer beads: Recent trends and developments in synthetic design and applications. Eur Polym J. Apr. 2011;47(4):542-59.

(56) References Cited

OTHER PUBLICATIONS

Vila et al., Customized Design of Magnetic Beads for Dynamic Magnetoresistive Cytometry. IEEE Trans Magn. Nov. 2014;50(11):4 pages.
Witters et al., Digital microfluidics-enabled single-molecule detection by printing and sealing single magnetic beads in femtoliter droplets. Lab Chip. Jun. 7, 2013;13(11):2047-54. doi: 10.1039/c3lc50119a.
EP 16749961.5, Jun. 12, 2018, Extended European Search Report.
PCT/US2016/017758, May 3, 2016, International Search Report and Written Opinion.
PCT/US2016/017758, Aug. 24, 2017, International Preliminary Report on Patentability.
Extended European Search Report for EP App. No. 16749961.5 dated Jun. 12, 2018.
Fang et al., Simple approach for ultrasensitive electrochemical immunoassay of Clostridium difficile toxin B detection. Biosensors and Bioelectronics. Mar. 15, 2014;53:238-44.
Oldfield et al., Clinical update for the diagnosis and treatment of Clostridium difficile infection. World Journal of Gastrointestinal Pharmacology and Therapeutics. Feb. 6, 2014;5(1):1-26.
Pollock et al., Differential Immunodetection of Toxin B from Highly Virulent Clostridium difficile BI/NAP-1/027. Journal of Clinical Microbiology. Feb. 25, 2015;53(5):1705-8.
Rissin et al., Multiplexed single molecule immunoassays. Lab On A Chip. 2013;13(15):2902-11.
Song et al., Development and Validation of Digital Enzyme-Linked Immunosorbent Assays for Ultrasensitive Detection and Quantification of Clostridium difficile Toxins in Stool. Journal of Clinical Microbiology. Jul. 22, 2015;53(10):3204-12.

\* cited by examiner

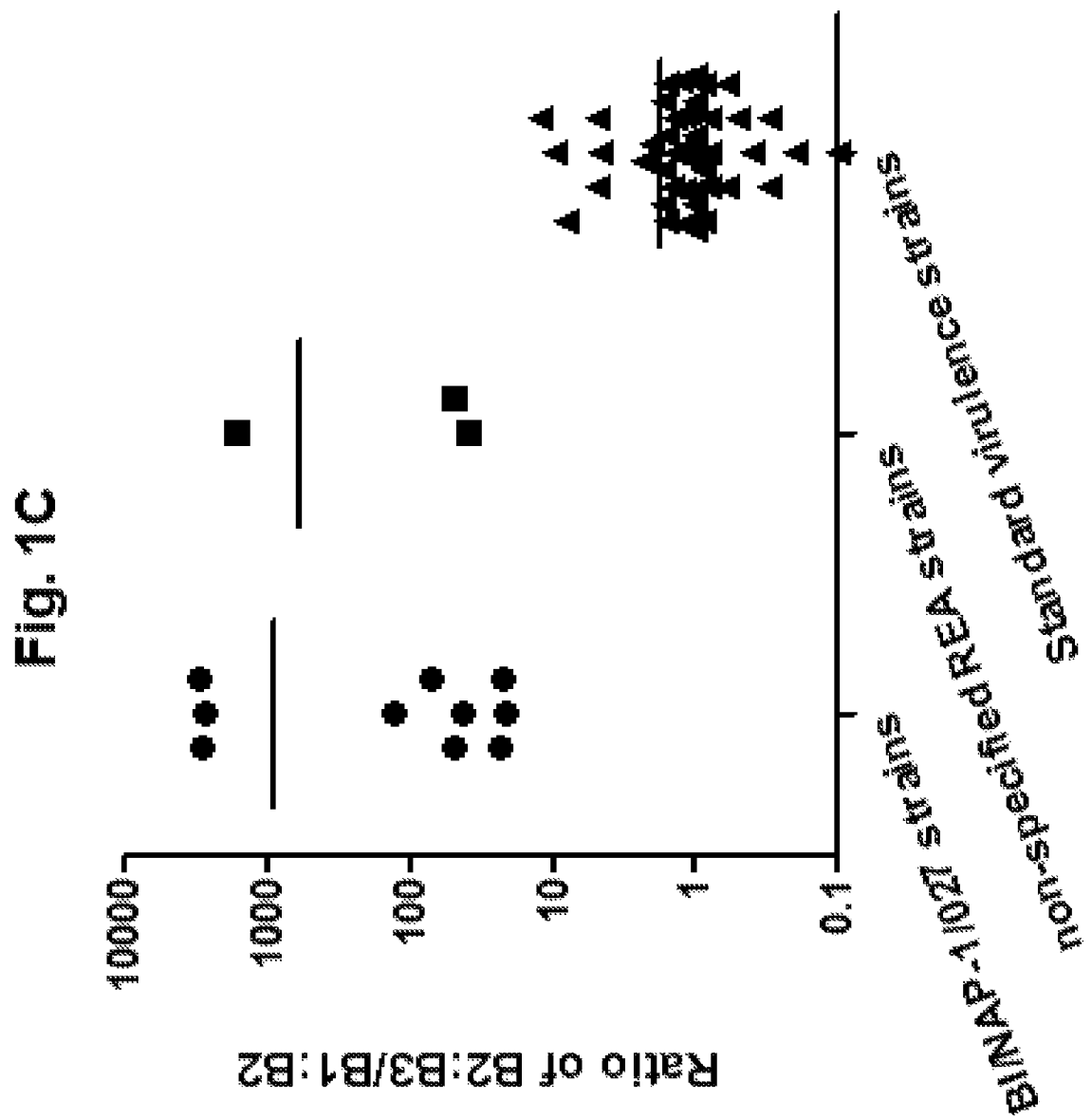

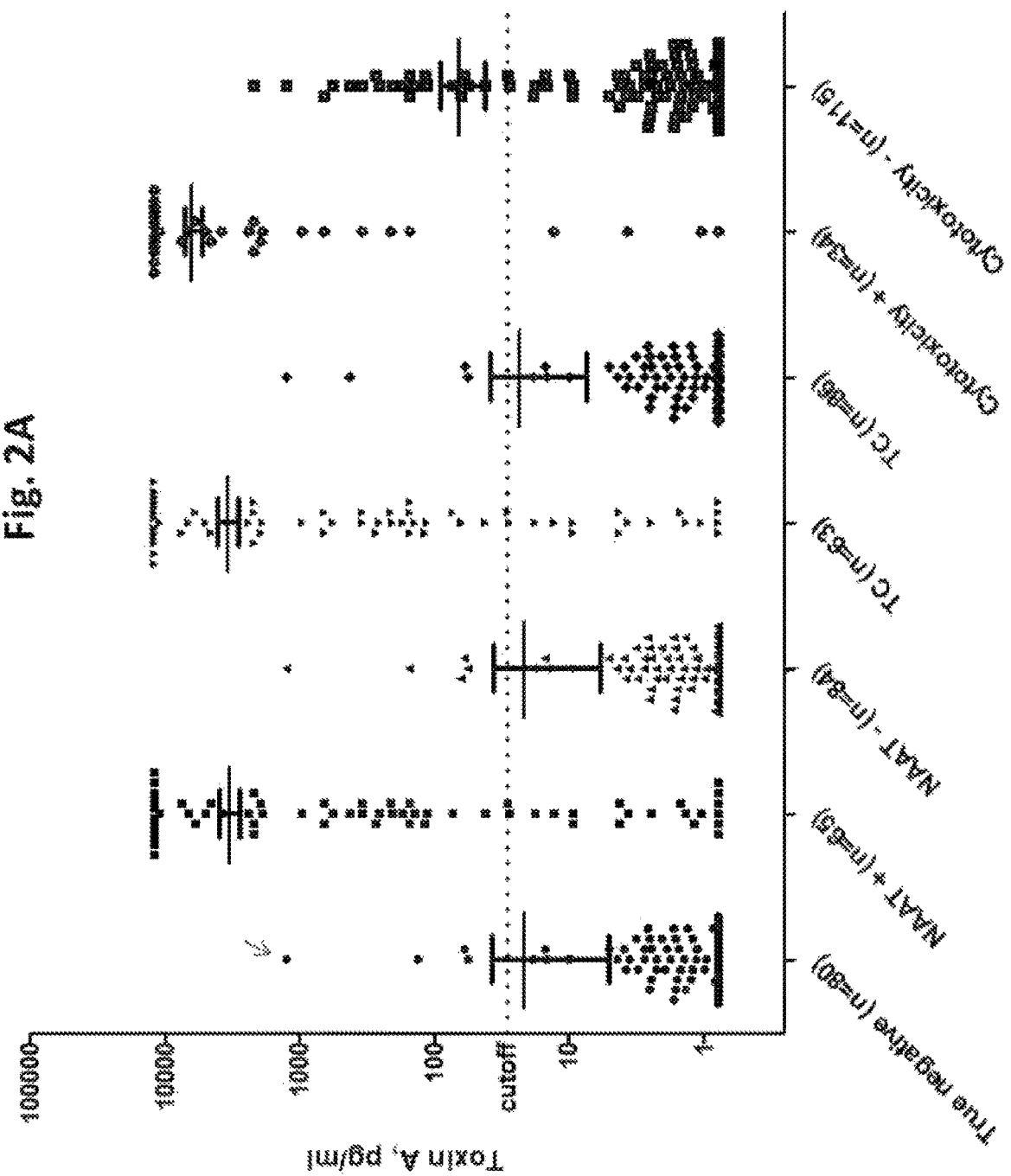

IMMUNOASSAYS FOR DIFFERENTIAL DETECTION OF CLOSTRIDIUM DIFFICILE

CROSS-REFERENCE TO RELATED APPLICATIONS

This application is a national stage filing under 35 U.S.C. § 371 of international application PCT/US2016/017758, filed Feb. 12, 2016, which claims priority under 35 U.S.C. § 119(e) to U.S. Provisional Application Ser. No. 62/116,073, filed Feb. 13, 2015, the contents of each of which are incorporated by reference herein in their entirety.

GOVERNMENT SUPPORT

This invention was made with government support under Grant No. 5 R21AI103612-02, awarded by the National Institutes of Health. The Government has certain rights in this invention.

BACKGROUND OF THE INVENTION

*C. difficile* is a significant nosocomial and community-acquired pathogen, associated with disease ranging from mild diarrhea to fatal pseudomembranous colitis. Cohen, et al., *Infect Control Hosp Epidemiol,* 2010. 31(5): p. 431-55. Since the turn of the millennium, rates of *C. difficile* infection (CDI) have increased globally, concomitant with increased rates of severe clinical presentations and worsened clinical outcomes. Cohen et al., 2010 and Burnham et al., *Clin Microbiol Rev,* 2013. 26(3): p. 604-30. CDI results from the production of two large protein exotoxins: toxins A (~308 kDa) and B (~270 kDa). Nontoxigenic strains are not pathogenic. While most strains produce both toxins A and B, a minority produce toxin B only. Toxins A and B are the primary virulence factors contributing to the pathogenesis of CDI, and the genes for these toxins (tcdA and tcdB) are co-located in a pathogenicity locus in toxigenic strains. Burnham et al., 2013 and Rupnik, *FEMS Microbiol Rev,* 2008. 32(3): p. 541-55.

Accurate diagnosis is critical for the effective management of *C. difficile* infection, but currently available diagnostics have major limitations. Despite mounting evidence that toxin detection is paramount for CDI diagnosis, conventional toxin immunoassays are insufficiently sensitive and cytotoxicity assays too complex. Assays that detect toxigenic organisms, including toxigenic culture (TC) and nucleic acid amplification testing (NAAT), are confounded by asymptomatic colonization by toxigenic *C. difficile*.

SUMMARY OF THE INVENTION

In aspect, the present disclosure provides a method for differentially detecting *C. difficile* based on virulence, the method comprising: (i) obtaining a sample comprising a *C. difficile* strain (e.g., obtained from a subject having or suspected of having *C. difficile* infection); (ii) performing a first immunoassay to detect toxin B of *C. difficile* in the sample, wherein the first immunoassay involves a first antibody and a second antibody, both of which bind toxin B of both highly virulent and less virulent *C. difficile* strains; (iii) performing a second immunoassay to detect toxin B of *C. difficile* in the sample, wherein the second immunoassay involves the second antibody and a third antibody, wherein the third antibody differentially binds toxin B of highly virulent *C. difficile* strains as relative to toxin B of less virulent *C. difficile* strains; (iv) comparing results obtained from step (ii) and step (iii); and (v) determining whether the sample comprises a highly virulent *C. difficile* strain or a less virulent *C. difficile* strain based on the comparing result of step (iv).

In some examples, the first immunoassay, the second immunoassay, or both are digital ELISA assays. Alternatively or in addition, either the first antibody or the second antibody in step (ii) may be conjugated to a label (e.g., biotin) and the other antibody may be immobilized on a solid support. The first immunoassay may further involves (a) a conjugate of streptavidin and an enzyme, and (b) a substrate of the enzyme, wherein the enzyme converts the substrate to a molecule that releases a detectable signal, such as a fluorescent signal.

In any of the differential detection methods described herein, the comparing step (iv) can be performed by calculating a ratio between a first value obtained from step (ii) and a second value obtained from step (iii), the first value representing the level of the toxin B detected in the first immunoassay and the second value representing the level of the toxin B detected in the second immunoassay.

In some embodiments, either the second antibody or the third antibody in step (iii) is conjugated to a label (e.g., biotin) and the other antibody is immobilized on a solid support. Alternatively or in addition, the second immunoassay may further involve (a) a conjugate of streptavidin and an enzyme, and (b) a substrate of the enzyme, wherein the enzyme converts the substrate to a molecule that releases a detectable signal, such as a fluorescent signal.

In any of the differential detection methods described herein, the third antibody is specific to toxin B of highly virulent *C. difficile* strains. In some examples, detection of toxin B in both the first immunoassay and the second immunoassay indicates that the sample comprises a highly virulent *C. difficile* strain; and detection of toxin B in the first immunoassay but not in the second immunoassay indicates that the sample comprises a less virulent *C. difficile* strain.

Alternatively, the third antibody is specific to toxin B of less virulent *C. difficile* strains. In some examples, detection of toxin B in the first immunoassay but not in the second immunoassay indicates that the sample comprises a highly virulent *C difficile* strain, and detection of toxin B in both the first immunoassay and the second immunoassay indicates that the sample comprises a less virulent *C. difficile* strain.

In some embodiments, the highly virulent strain is a BI/NAP-1/027 strain, a ribotype 078/BK strain, or a ribotype 244/AF strain.

In some embodiments, the sample (e.g., a stool sample) is obtained from a subject having or suspected of having *C. difficile* infection. In some examples, the method may further comprise determining whether or not the subject is infected with a highly virulent *C difficile* strain.

In another aspect, the present disclosure provides a kit for differentially detecting *C. difficile* based on virulence, the kit comprising: (i) a first pair of anti-toxin B antibodies including a first antibody and a second antibody, wherein the first antibody and the second antibody bind toxin B of both highly virulent and less virulent *C. difficile* strains; and (ii) a second pair of anti-toxin B antibodies, including the second antibody and a third antibody, which differentially binds toxin B of highly virulent *C. difficile* strains as relative to toxin B of less virulent *C. difficile* strains. In the first pair of anti-toxin B antibodies, either the first antibody or the second antibody may be conjugated to a label (e.g., biotin) and the other antibody may be immobilized on a solid support. Alternatively or in addition, in the second pair of anti-toxin B antibodies, either the second antibody or the third antibody may be conjugated to a label (e.g., biotin) and the other antibody may be immobilized on a solid support.

In some examples, the kit may further comprise a conjugate of streptavidin and an enzyme, and optionally a substrate of the enzyme, wherein the enzyme converts the substrate to a molecule that releases a detectable signal, e.g., a fluorescent signal.

Any of the kits described herein may further comprise instructions for carrying out a method set forth in any of the differential detection methods described herein.

In yet another aspect, the present disclosure provides a method for detecting *C. difficile*, comprising: (i) providing a sample suspected of having a *C difficile* strain; (ii) detecting toxin B of the *C difficile* by digital ELISA; (iii) detecting toxin A of the *C difficile* by digital ELISA; and (iv) assessing presence of a toxigenic *C difficile* strain and/or a toxin thereof in the sample based on the result of step (ii), the result of step (iii), or a combination thereof. In some embodiments, the level of toxin B detected in step (ii) higher than 20 pg/ml indicates that the sample contains a toxigenic *C. difficile* strain or a toxin thereof.

Also within the scope of the present disclosure is a method for diagnosing *C. difficile* infection in a subject, comprising: (i) examining whether the subject manifests a symptom associated with *C. difficile* infection (e.g., diarrhea); (ii) detecting the presence of toxin A, toxin B, or both in a sample obtained from the subject; and (iii) determining whether the subject has *C. difficile* infection. The method may further comprise detecting the presence of a nucleic acid that encodes toxin A, a nucleic acid that encodes toxin B, or both, in a sample obtained from the subject.

In some embodiments, step (ii), step (iii), or both are performed by a digital ELISA. Alternatively or in addition, step (ii) is performed by a differential detection method to determine whether the sample contains a highly virulent strain or a less virulent strain.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1C is a diagram showing a comparison of ratios of signals from B2/B3 vs B1/B2 digital ELISAs, as measured in clinical stool samples yielding the isolates (via toxigenic culture) in the following three groups: BI/NAP-1/027 strains (n=10), "non-specified REA" strains including one from Group AF (n=3), and all other strains recovered (noted here as "standard virulence," as none of the types have been particularly associated with hypervirulence). Horizontal bars indicate the mean for each group.

FIG. 2A is a diagram showing a graph of the digital ELISA results for groups of samples testing positive vs. negative on other assays for toxin A. One of the 80 "true negative" samples was excluded from the cutoff calculation because it was an extreme outlier in the toxin A assay. Mean signals in each group are indicated by horizontal lines. The calculated clinical cutoffs for each digital ELISA (29.4 pg/mL for the toxin A assay) are shown as dotted lines spanning the figure. The arrow indicates a sample that was excluded from calculation of the cutoff because it was an extreme outlier and substantially distorted the mean for that assay. NAAT, nucleic acid amplification testing; TC, toxigenic culture.

DETAILED DESCRIPTION OF THE INVENTION

Figure 1A:
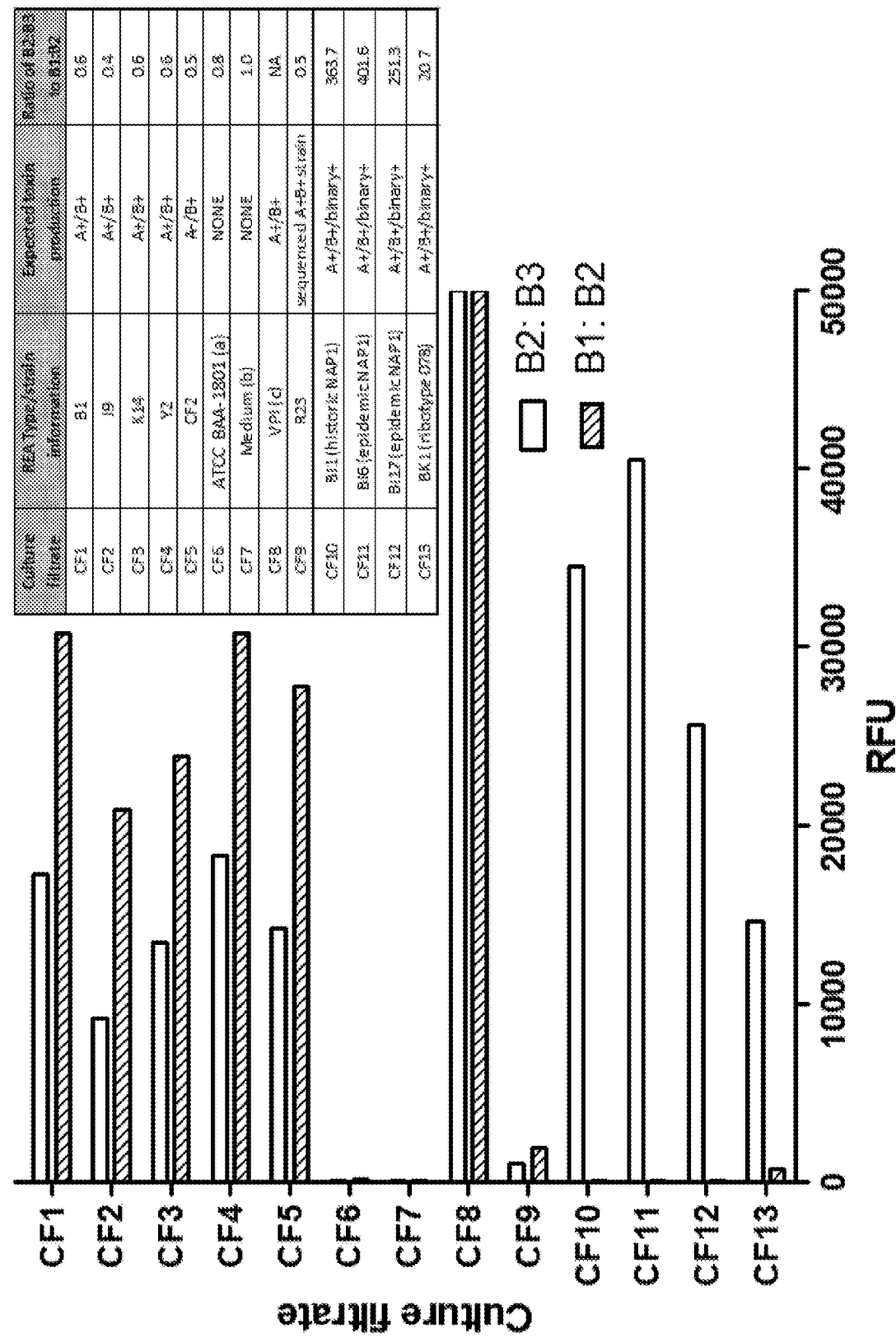
FIG. 1A is a chart showing the comparison of toxin B levels in culture filtrates prepared from a panel of *C. difficile* isolates (table inset), as measured by conventional ELISA using the B2/B3 antibody pair (white bars) vs the B1/B2 antibody pair (hatched bars). Ratios presented for each culture filtrate are ratios of the signals measured using the two different assays. CF, culture filtrate; REA, Restriction Endonuclease Analysis.

The recent increase in global incidence and severity of *Clostridium difficile* infection (CDI) [1-3] is of major concern. CDI, ranging from mild antibiotic-associated diarrhea to lethal pseudomembranous colitis, consumes an increasing proportion of resources for diagnosis, treatment, and infection control in both adult and pediatric populations [2, 4]. A recent US prevalence survey of health care-associated (HCA) infections [5] found that *C. difficile* was the most commonly reported pathogen, causing 12.1% of HCA infections. Despite available therapies, treatment failure and relapse are common [1, 2, 6]. The emergence of epidemic strains capable of toxin hyper-production and increased disease severity/mortality [2, 7, 8] has further increased the urgency of improving methods for diagnosis and treatment. Accurate diagnosis remains the cornerstone of effective management.

Disease caused by *C. difficile* is due to production of two large protein exotoxins: toxins A and B [9, 10]; nontoxigenic strains are not considered to be pathogenic [11]. These high molecular weight protein exotoxins (308 and 270 kDa, respectively) are immunologically and biologically distinct. Most strains produce both toxins A and B, though there are a minority of strains that produce B only (e.g. [12, 13]); the genes for these toxins (tcdA and tcdB) are co-located in a pathogenicity locus in toxigenic strains [11, 14].

While the presence of toxin is necessary for disease, the optimal method for diagnosis of CDI remains controversial. The classic gold standard stool assay, toxigenic culture (TC), is complex, lengthy, and unstandardized; furthermore, it is increasingly recognized that detection of a toxigenic organism, rather than the toxin itself, is suboptimal. Despite arguments that detection of toxin in stool has highest clinical specificity and predictive value [2, 15, 16], the field has rapidly moved towards nucleic acid amplification testing (NAAT), for ultrasensitive detection of toxigenic organisms. However, studies have repeatedly reported NAAT-positive individuals who clinically did not have CDI [17-20], and the field is increasingly recognizing that the utility of NAAT (like TC) is confounded by asymptomatic colonization by toxigenic C. difficile [19, 21-23]. Furthermore, the presence of the toxin genes also does not necessarily correlate to gene expression [14, 24]. Thus, by detecting C. difficile organisms (potentially including even transient environmental spores), rather than toxins A and B which are the known effectors of disease, NAAT lacks specificity for clinical disease [2].

Despite mounting evidence that toxin detection is paramount for CDI diagnosis, current methods for toxin detection remain inadequate. While cytotoxicity assay can have good analytical sensitivity for toxin B [limit of detection (LOD) 1-10 pg/mL for toxin spiked into buffer [25]], this assay (like TC) is laborious, slow, and unstandardized. Conventional qualitative toxin immunoassays are widely used [2], but have high LODs (e.g. ~0.8-2.5 ng/mL) [26, 27] and poor sensitivity (52-75% vs TC [28, 29]). Given these limitations, the field is poised for a simple toxin detection test that combines high analytical sensitivity with the clinical specificity of toxin detection. The fact that disease severity has been correlated to toxin levels in the host in preliminary studies [30, 31] further suggests that the ability to simply and reliably quantify toxin levels in stool could be clinically valuable to predict disease and treatment outcomes, and in identifying those who need aggressive therapy.

The present disclosure provides highly sensitive and/or quantitative methods for detection of toxin A, toxin B, or both of C. difficile, including methods that allow for differential detection of toxin B polypeptides from C. difficile strains having different leveled virulence (e.g., highly virulent or less virulent). Such assay methods may involve digital ELISA based on single molecule array (Simoa) technology. [Rissin, et al., Nat Biotechnol, 28(6): p. 595-9 (2010); Rissin, et al., Anal Chem, 83(6): p. 2279-85 (2011); and Kan, et al., Lab Chip, 2012. 12(5): p. 977-85.] These detection methods can be applied in clinical settings for diagnosing C. difficile, either alone or in combination with one or more other diagnostic approaches known in the art or described herein. The assays described herein have high analytical sensitivity and specificity, and detect toxin directly, thereby providing higher diagnostic accuracy over existing assays. Further, the results obtained from such assays, for example, the differential detection assay for identifying highly virulent strains versus less virulent strains, can help determine suitable approaches for treating C. difficile infection based on the level of virulence of the involved C. difficile strain.

Any one of the detection assays described herein can be performed using a suitable detecting system or device, such as Simoa™ and Simoa HD-1 Analyzer™ provided by Quanterix.

Differential Detection Assays

One aspect of the present disclosure provides differential detection assays, which allows for distinguishing highly virulent C. difficile strains from those that are less virulent.

There are at least 25 C. difficile "toxinotypes" (i.e., groups of strains defined by changes in the genetic locus (PaLoc) encoding toxins A and B), including a reference strain (VPI 10463, or "toxinotype 0") [Rupnik., FEMS Microbiol Rev, 32(3): p. 541-55 (2008)]. There are two types of "variant" toxinotypes: those with variations in the toxin genes themselves (as defined by RFLP-PCR), and those with variations in toxin production (i.e., producing only toxin B, or producing binary toxin (an additional toxin with unclear function)). Variant toxins may differ from wild-type toxins in size, substrate specificity, in vitro and in vivo activity, and immunoreactivity. [Rupnik, FEMS Microbiol Rev, 32(3): p. 541-55 (2008)]. The sensitivity of EIA tests [vs. toxigenic culture (TC)] performed on stool has been reported to vary with C. difficile ribotype [Tenover, et al., J Clin Microbiol, 48(10): p. 3719-24 (2010)], whereas sensitivity of PCR testing in the same study did not vary with ribotype.

Different C. difficile strains vary in toxin production with respect to type, level, or both. Multiple studies suggested a correlation between stool toxin concentrations and disease severity [e.g., Burnham, et al., Clin Microbiol Rev, 26(3): p. 604-30 (2013); and Planche, et al., Lancet Infect Dis, 13(11): p. 936-45 (2013)]. Consistent with this finding, a recently emerged epidemic strain, BI/NAP-1/027 (toxinotype IIIb) (henceforth "BI") is notable for its higher toxin yields in vitro (about 20-fold higher than toxinotype 0 strains [Warny, et al., Lancet, 366(9491): p. 1079-84 (2005)]), deletions in a putative negative regulator for toxins A and B (tcdC), and its ability to cause unusually severe and recurrent disease [Cohen, S. H. et al., Infect Control Hosp Epidemiol, 31(5): p. 431-55 (2010); Warny, M. et al., Lancet, 366(9491): p. 1079-84 (2005); Loo, V. G. et al., N Engl J Med, 353(23): p. 2442-9 (2005)].

In addition to BI/NAP-1/027 strains, other emergent strains have been associated with particularly severe disease, including the ribotype 078/BK group [Goorhuis, et al., Clin Infect Dis, 47(9): p. 1162-70 (2008)] and the ribotype 244/AF group [Lim, et al., Clin Infect Dis, (2014)].

Identifying or excluding highly virulent strains is relevant to therapeutic decision-making; two Phase III clinical trials demonstrated that fidaxomicin (vs. vancomycin) achieved significantly lower recurrence rates for CDI associated with non-BI strains [Louie, et al., N Engl J Med, 364(5): p. 422-31 (2011)]). However, other than molecular testing, the highly virulent BI strains are not easily identified by routine laboratory testing [Rupnik, M., FEMS Microbiol Rev, 32(3): p. 541-55 (2008)].

The differential detection methods described herein may involve one or more immunoassays to detect the presence or determine the level (quantity) of toxin B or toxin A of C. difficile in a sample having or suspected of containing C. difficile cells using at least one antibody that differentially binds a toxin B or toxin A polypeptide from a highly virulent C. difficile strain as relative to a less virulent strain. Highly virulent C. difficile strains (also known as hypervirulent strains) are those that are capable of inducing severe clinical courses, increased mortality, and recurrent infections. Examples include, but are not limited to, BI/NAP-1/027 strains, ribotype 078/BK group strains, and ribotype 244/AF group strains. Less virulent C. difficile strains are those that may cause clinical courses at a moderate level. Non-virulent C. difficile strains are those that do not have pathogenic effects. Examples of less virulent strains include, but are not limited to, strains from the CF group, Y group, DH group, and J group. See FIG. 1B. The level of virulence of a *C. difficile* strain can be determined by clinical studies associating the particular *C. difficile* strain with disease severity following routine medical practice. Disease severity may be defined by death, ICU admission, or colectomy within 40 days of stool testing.

(I) Antibodies Having Differential Binding Specificities to Toxin B or Toxin A

An antibody (interchangeably used in plural form) is an immunoglobulin molecule capable of specific binding to a target, such as toxin A or toxin B of a *C. difficile* strain, through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The antibodies described herein can be murine, rat, human, or any other origin (including chimeric or humanized antibodies).

In some embodiments, the anti-toxin B antibodies described herein (or anti-toxin A antibodies described below) have a suitable binding affinity to the antigen. As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

$$[Bound]=[N][Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, which is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the antibodies used in the detection assays described herein differentially bind toxin B or toxin A of highly virulent *C. difficile* strains as compared with toxin B (or toxin A) of less virulent *C. difficile* strains. An antibody that "differentially binds" to a first target or a first epitope as relative to a second target or a second epitope refers to an antibody that has different binding affinities to the first and second targets or different binding affinities to the first and second epitopes. In some examples, such an antibody may have a much higher binding affinity to the first target/epitope as relative to the second target/epitope, or vice versa, e.g., at least 2-fold, 5-fold, 10-fold, 50-fold, 100-fold, 200-fold, 500-fold, 1,000-fold, 10,000-fold higher. In other examples, the antibody may have a much lower binding affinity to the first target/epitope as relative to the second target/epitope, or vice versa, e.g., at least 2-fold, 5-fold, 10-fold, 50-fold, 100-fold, 200-fold, 500-fold, 1,000-fold, 10,000-fold lower.

In specific examples, the antibodies used in the detection assays described herein specifically bind toxin B or toxin A of a highly virulent *C. difficile* strain. Alternatively, the antibodies specifically bind toxin B or toxin A of a less virulent *C. difficile* strain. An antibody "specifically binds" to a target antigen if it binds with greater affinity, avidity, more readily, and/or with greater duration than it binds to other substances. For example, an antibody that specifically (or preferentially) binds to toxin B or toxin A of highly virulent *C. difficile* strains is an antibody that binds this target antigen with greater affinity, avidity, more readily, and/or with greater duration than it binds to other antigens, such as toxin B or toxin A of less virulent *C. difficile* strains. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding. In some examples, the antibodies used in the assay methods described herein bind toxin B or toxin A of a highly virulent *C. difficile* strain but not toxin B or toxin A of less virulent *C. difficile* strains, e.g., binding to an epitope that is distinct in toxin B or toxin A of highly virulent *C. difficile* strains. In other examples, the antibodies used in the assay methods described herein bind toxin B or toxin A of a less virulent *C. difficile* strain but not toxin B or toxin A of highly virulent

*C. difficile* strains, e.g., binding to an epitope that is distinct in toxin B or toxin A of less virulent *C. difficile* stains.

The detection methods described herein may also involve antibodies that bind toxin B or toxin A of a broad spectrum of *C. difficile*, regardless of virulence levels.

Antibodies capable of binding toxin B or toxin A of *C. difficile* strains with different virulence levels can be made by any method known in the art. See, for example, Harlow and Lane, (1988) Antibodies: A Laboratory Manual, Cold Spring Harbor Laboratory, New York.

In some embodiments, antibodies differentially binding (e.g., specific to) a target antigen (e.g., toxin B/toxin A of a highly virulent *C. difficile* strain or toxin B/toxin A of a less virulent *C. difficile* strain) can be made by the conventional hybridoma technology, using a suitable antigen. Sequences of toxin B or toxin A of different *C. difficile* strains are known in the art. Some examples are provided in the tables 1 and 2 below.

TABLE 1

Toxin B of Exemplary *C. difficile* strains

| *C. difficile* Strains | GenBank Accession Number for Toxin B |
|---|---|
| BI1 | YP_006197785.1 |
| F253 | WP_021407033.1 |
| P59 | WP_021426110.1 |
| CD160 | WP_021383384.1 |
| F314 | WP_021407773.1 |
| CD69 | WP_021374582.1 |
| E19 | CCL40218.1 |
| CD45 | WP_021371861.1 |
| 70-100-2010, CD41, CD104, CD206, CD212, E12 | WP_003434531.1 |
| DA00211 | WP_021402343.1 |
| P48, P70, P73, P 75 | WP_021424365.1 |
| P13, P46, P68 | WP_021418418.1 |
| T6 | CCL51870.1 |
| 630 | WP_009902069.1 |
| P11 | WP_021418106.1 |
| P7 | WP_021417070.1 |
| CD8, CD9, P5, P37 | WP_021360236.1 |
| NAP07, T5, T20, E1 | WP_003418170.1 |
| DA00305 | WP_021405616.1 |
| DA00129, CD86 | WP_021377046.1 |
| CD129 | WP_021380256.1 |
| DA00216 | WP_021403734.1 |
| CD43, CD131, CD149, CD166, CD200, F152, P8, P69 | WP_021370125.1 |
| CD113 | WP_021378956.1 |
| 050-P50-2011, 002-P50-2011 | WP_003426838.1 |
| Y184 | EQI47082.1 |
| T14 | CCL93631.1 |
| CD40 | EQE46098.1 |
| 840 | WP_021391274.1 |
| P3 | EQI94941.1 |
| DA00232 | EQH37808.1 |
| CD201 | EQF71112.1 |
| CD201 | EQF71113.1 |
| CD196, R20291 | WP_009892729.1 |
| P13 | WP_021418419.1 |
| Y41 | WP_021411551.1 |
| CD181 | WP_021388614.1 |
| 655 | WP_021390804.1 |
| DA00114 | WP_021393724.1 |
| 630 | WP_011860904.1 |
| DA0023, DA00261 | WP_021401850.1 |
| DA00197 | WP_021398198.1 |
| P25, DA00244 | WP_021404260.1 |
| P5 | EQJ00853.1 |
| CD9 | WP_021361364.1 |
| P1 | WP_021415976.1 |
| DA00129, F152 | WP_021394767.1 |
| P59 | WP_021426113.1 |

TABLE 1-continued

Toxin B of Exemplary *C. difficile* strains

| *C. difficile* Strains | GenBank Accession Number for Toxin B |
|---|---|
| Y266 | WP_021413482.1 |
| CD42 | WP_021369285.1 |
| CD17 | WP_021362272.1 |
| CD70 | WP_021376831.1 |
| CD159 | WP_021381998.1 |
| P32 | WP_021422924.1 |
| P69 | WP_021427085.1 |
| CD111, DA00128 | WP_021378690.1 |
| DA00191 | WP_021400350.1 |
| P31 | WP_021422850.1 |
| P73 | WP_021427542.1 |
| Y247 | WP_021413325.1 |
| CD90, DA00167, 842 | WP_021377621.1 |
| CD166 | WP_021386968.1 |
| CD8 | EQE15594.1 |
| P72 | WP_021427279.1 |

TABLE 2

Toxin A of Exemplary *C. difficile* strains

| *C. difficile* Strains | GenBank Accession Number for Toxin A |
|---|---|
| ATCC 4325/VPI 10463 | P16154 |
| ST37 | AGG91507 |
| JF09 | AFN52237 |
| BI1 | YP_006197787 |
| R20291 | YP_003217088 |

The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-toxin B or anti-toxin A monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of binding to toxin B or toxin A. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in a vector in a host cell and the host cell can then be expanded and frozen for future use. In an alternative, the polynucleotide sequence may be used for genetic manipulation to improve the affinity (affinity maturation), or other characteristics of the antibody. It may be desirable to genetically manipulate the antibody sequence to obtain greater affinity to the target antigen as relative to other antigens. It will be apparent to one of skill in the art that one or more polynucleotide changes can be made to the antibody and still maintain its binding specificity to the target antigen.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Genetically engineered antibodies, such as humanized antibodies, chimeric antibodies, single-chain antibodies, and bi-specific antibodies, can be produced via, e.g., conventional recombinant technology.

In some embodiments, the full-length of toxin B or toxin A of a highly virulent *C. difficile* strain or toxin B or toxin A of a less virulent *C. difficile* strain, or a fragment thereof, can be used as the antigen for preparing antibodies binding to such, following methods known in the art or described herein. Antibodies thus obtained can be characterized using methods well known in the art, for example, to confirm its binding activity to the antigen. Such antibodies can then be characterized for their binding activities to toxin B or toxin A of a different *C. difficile* strain, e.g., a strain having a different virulence level. For example, if toxin B or toxin A of a highly virulent *C. difficile* strain is used as the antigen for antibody production, the antibodies thus obtained that bind the toxin B or toxin A of a highly virulent *C. difficile* strain can be characterized for their binding activity/affinity to toxin B or toxin A of less virulent *C. difficile* strains. Alternatively, if toxin B or toxin A of a less virulent *C. difficile* strain is used as the antigen for antibody production, the antibodies thus obtained that bind the toxin B or toxin A can be characterized for their binding activity/affinity to toxin B or toxin A of highly virulent *C. difficile* strains. Antibodies that differentially bind toxin B or toxin A of highly virulent *C. difficile* strains as relative to toxin B or toxin A of less virulent *C. difficile* strains can thus be identified.

Alternatively, a fragment that comprises an epitope that presents only in toxin B or toxin A of highly virulent *C. difficile* strains or an epitope that presents only in toxin B or toxin A of less virulent *C. difficile* strains can be used as the antigen for antibody production. Antibodies thus produced can be characterized to confirm their differential binding activity to toxin B or toxin A of highly virulent *C. difficile* strains versus toxin B or toxin A of less virulent *C. difficile* strains. Such highly virulent strain-specific or less virulent strain-specific epitopes can be identified by comparing the amino acid sequences of toxin B or toxin A polypeptides from different *C. difficile* strains, e.g., those listed in Table 1 above, by conventional methods (e.g., computational analysis).

Any of the antibodies described herein may be prepared by culturing a hybridoma cell line producing such and purifying the antibodies from the hybridoma culture. Alternatively, they may be produced by recombinant technology.

As a further alternative, antibodies may be produced that bind toxins (e.g., toxin A or toxin B) from a broad range of *C. difficile* strains, including both highly virulent and less virulent strains. For example, fragments containing an epitope present in a toxin of both highly virulent and less virulent strains may be used to produce antibodies. Antibodies capable of binding such can be selected via routine methods. Such antibodies can be further confirmed for their binding activity to toxins of both highly virulent and less virulent strains.

In one example, DNA encoding a monoclonal antibody specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library. scFv clones specific to toxin B of a highly virulent *C. difficile* strain or toxin B of a less virulent *C. difficile* strain can be identified from the library following routine procedures. Positive clones can be subjected to further screening to identify those that differentially bind toxin B of highly virulent strains as relative to toxin B of less virulent strains.

Antibodies obtained following a method known in the art or described herein can be characterized using methods also known in the art or described herein. For example, one method is to identify the epitope to which the antigen binds, also referred to as "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. As an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. As an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the toxin B (or toxin A) polypeptide have been replaced (swapped) with sequences from a closely related, but antigenically distinct protein (such as a toxin B of a different *C. difficile* strain). By assessing binding of the antibody to the mutant toxin B, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Any of the suitable methods known in the art, e.g., the epitope mapping methods as described herein, can be applied to determine whether the antibody binds one or more of the specific residues/segments in a toxin B or toxin A polypeptide as described herein. Further, the interaction of the antibody with one or more of those defined residues in the antigen can be determined by routine technology.

(II) Immunoassays

One or more immunoassays can be performed, using any of the antibodies described herein that differentially binds toxin B or toxin A of highly virulent *C. difficile* strains as relative to toxin of less virulent *C. difficile* strains, to determine the presence of highly virulent *C. difficile* or less virulent *C. difficile* in a sample, e.g., a biosample obtained from a subject such as a human patient having or suspected of having *C. difficile* infection.

An immunoassay is a biochemical test that measures the presence or concentration of a molecule of interest (e.g., a macromolecule such as a protein) in a sample through the use of an antibody or immunoglobulin. Typically, an antibody specific to the molecule of interest interacts with the molecule in an immunoassay. The antibody can be labeled, directly or indirectly such that those bound to the molecule could release a detectable signal. Presence or concentration of the molecule of interest can be determined based on the level of the detectable signal. The immunoassay described herein can involve the use of different types of labels, including enzymes, radioactive isotopes, DNA reporters, fluorogenic reporters, electrochemiluminescent tags, all of which are well known in the art. In some instances, the immunoassay can involve a catalyst such as an enzyme to amplify the signal. Alternatively, the immunoassay described herein can be performed without the use of a label.

The "immunoassay" used to detect an antigen of interest (e.g., toxin B or toxin A) according to the present disclosure may be based on standard techniques known in the art. The immunoassay as described herein may be in various formats, e.g., competitive, one-site non-competitive, or two-site, non-competitive (Sandwich assays). In some examples, it may comprise multiple steps with reagents being added and washed away or separated at different points in the assay. Such an assay is known as a heterogeneous immunoassay. In other examples, the immunoassay may be carried out simply by mixing the reagents and sample and making a physical measurement. Such assays are known as homogenous immunoassays.

In a preferred embodiment, the immunoassay may be an ELISA, which may be performed based on single molecule array (Simoa) technology as described herein. See also Rissin, et al., Nat Biotechnol, 28(6): p. 595-9 (2010); Rissin, et al., Anal Chem, 83(6): p. 2279-85 (2011); Kan, et al., Lab Chip, 2012. 12(5): p. 977-85. In digital ELISAs, single protein molecules are captured on paramagnetic beads, labeled with an enzyme, and detected in arrays of femtoliter-sized wells. Sensitivities of digital ELISAs are typically 1000-fold greater than conventional ELISAs. In applying Simoa to the development of digital immunoassays for toxins A and B, the differential binding of toxin B of BI/NAP-1/027 and BK/078 strains by specific pairs of candidate monoclonal antibodies against toxin B was observed. It is shown that the disclosed immunoassays can differentiate toxin Bs of highly virulent strains from those of other *C. difficile* isolates, and thus can provide information that is highly relevant to clinical prognosis.

ELISAs are generally well known in the art. The ELISA assay used in the detection methods described herein can be in any format known in the art, including direct ELISA, Sandwich ELISA, competitive ELISA, and multiple and ready-to-use ELISA. In a typical "indirect" ELISA, an antibody having specificity for the antigen of interest is immobilized on a solid surface (e.g., the wells of a standard microtiter assay plate, or the surface of a microbead or a microarray) and a sample comprising, e.g., bodily fluid or substances extracted from stool samples, to be tested for the presence of the antigen is brought into contact with the immobilized antibody. Any antigen of interest in the sample will bind to the immobilized antibody. The bound antibody/antigen complexes may then be detected using any suitable method. In one embodiment, a second antibody, which specifically recognizes an epitope of the antigen, which may be different from the epitope recognized by the immobilized antibody, is used to detect the antibody/antigen complexes. The second antibody is usually labelled with a detectable marker (directly or indirectly). In some examples, the maker can be an enzyme such as peroxidase, alkaline phosphatase, or galactosidase, allowing quantitative detection by the addition of a substrate for the enzyme which generates a detectable product, for example a colored, chemiluminescent or fluorescent product. Other types of detectable labels known in the art may be used with equivalent effect. In other examples, the second antibody may be labeled with a member of a receptor/ligand pair, for example, biotin. An enzyme conjugate comprising an enzyme conjugated with the other member of the receptor/ligand pair, e.g., streptavidin, can be brought into contact with the second antibody. A substrate of the enzyme is then added to produce a product that releases a detectable signal.

In some embodiments, a differential detection method as described herein involves two immunoassays, one or both of which may be digital ELISAs. The first immunoassay may comprise a pair of antibodies capable of binding to C. difficile toxin B or toxin A, one being a capture antibody and the other being a detection antibody. Both the capture and detection antibodies may bind to toxin B or toxin A of a broad spectrum of C. difficile strains such that toxin B or toxin A of both highly virulent strains and less virulent strains can be detected/quantified in the first immunoassay. In a preferred example, the capture and detection antibodies bind to two separate epitopes of the toxin B or toxin A.

The second immunoassay may comprise a pair of antibodies, one of which differentially binds to toxin B or toxin A of highly virulent C. difficile strains as relative to toxin B or toxin A of less virulent strains. The other antibody may bind to toxin B or toxin A of a broad spectrum of C. difficile strains, regardless of their virulence levels. In some instances, this antibody may be identical to the capture or detection antibody used in the first immunoassay. The differential binding antibody can be used as the detection antibody and the other antibody can be used as the capture antibody, or vice versa. In some examples, the differential binding antibody is specific to toxin B of highly virulent C. difficile strains (e.g., it has a higher binding affinity to toxin B or toxin A of highly virulent C. difficile strains as compared with its binding affinity to toxin B or toxin A of less virulent strains or it does not bind toxin B or toxin A of less virulent C. difficile strains) and the second immunoassay allows for detection or quantification of toxin B or toxin A of highly virulent C. difficile strains. In other examples, the differential binding antibody is specific to toxin B or toxin A of less virulent C. difficile strains (e.g., it has a higher binding affinity to toxin B or toxin A of less virulent C. difficile strains as compared with its binding affinity to toxin B or toxin A of highly virulent strains or it does not bind to toxin B or toxin A of highly virulent C. difficile strains) and the second immunoassay allows for detection or quantification of toxin B or toxin A of less virulent C. difficile strains.

By comparing the results obtained from the first and second immunoassays, the presence of a highly virulent C. difficile strain or a less virulent C. difficile strain can be determined. For example, if an antibody specific to toxin B of highly virulent strains is used in the second immunoassay, positive results from both the first immunoassay and the second immunoassay indicate that the sample contains a highly virulent strain, while positive results from the first immunoassay and negative results from the second immunoassay indicate that the sample contains a less virulent strain. Alternatively, if an antibody specific to toxin B of less virulent strains is used in the second immunoassay, positive results from both the first immunoassay and the second immunoassay indicate that the sample contains a less virulent strain, while positive results from the first immunoassay and negative results from the second immunoassay indicate that the sample contains a highly virulent strain. If negative results are observed in both the first and second immunoassays, it indicates that the sample may contain no C. difficile or a non-virulent strain.

In some examples, a ratio between a first value obtained from the first immunoassay and a second value obtained from the second immunoassay can be calculated. The first value (e.g., relative fluorescent units) represents the level of toxin B or toxin A measured in the first immunoassay and the second value (e.g., relative fluorescent units) represents the level of toxin B or toxin A measured in the second immunoassay. This ratio can be compared with a predetermined value to determine the presence of a highly virulent C. difficile strain or a less virulent C. difficile strain in a sample that is analyzed by the differential detection method described herein. The predetermined value represents a cutoff value, which can be determined by performing the same assay on samples containing a standard highly virulent strain and/or samples containing a standard less virulent strain.

Figure 4:
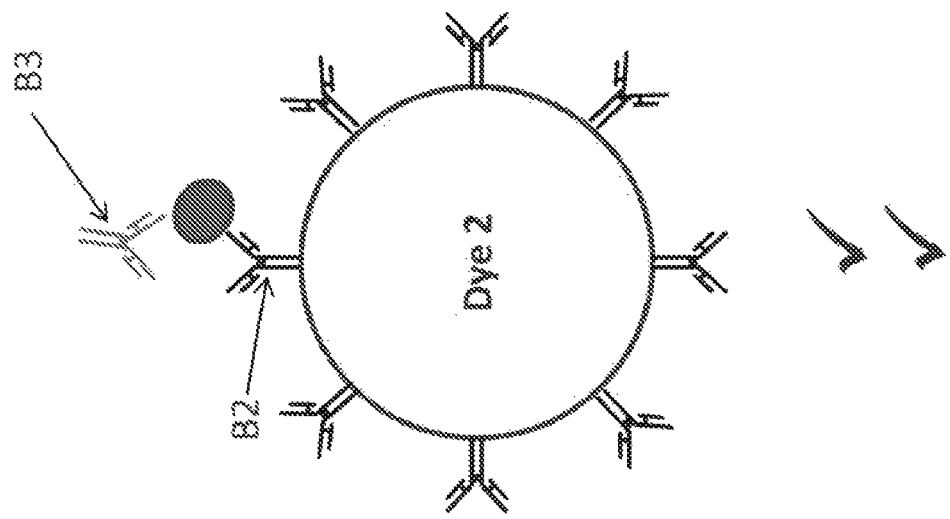
FIG. 4 is a schematic illustration showing a representative multiplex assay for differentially detecting a toxin such as toxin B from a highly virulent *C. difficile* strain (NAP 1) relative to the toxin from a less virulent *C. difficile* strain.
Figure 4:
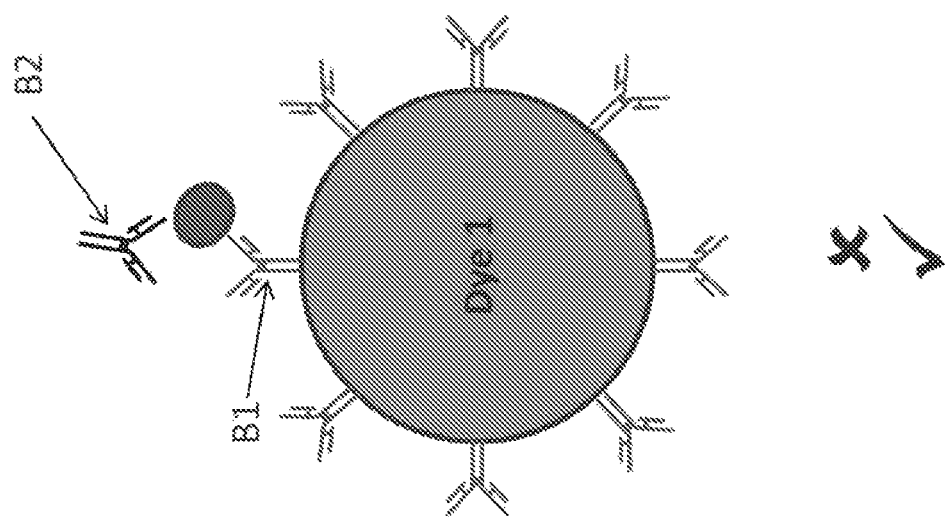
Figure 5:
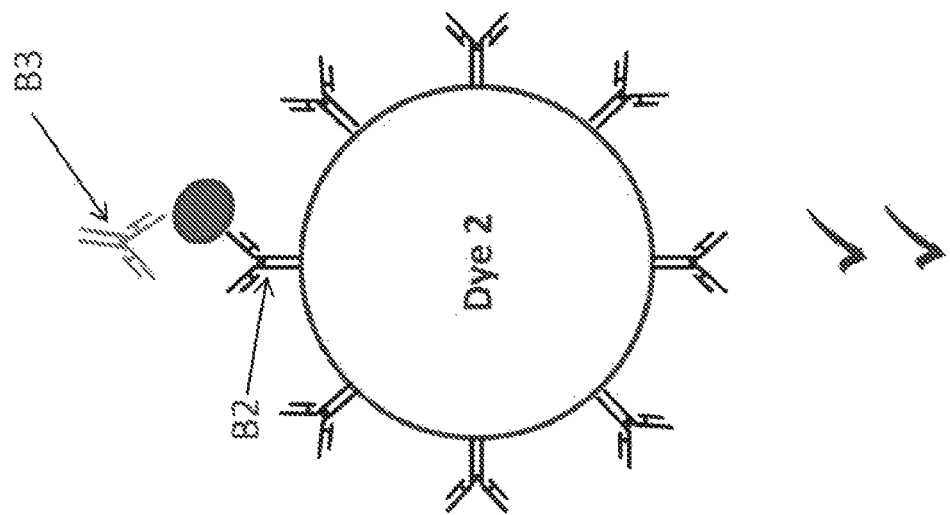
FIG. 5 is a schematic illustration showing a representative simplified assay with a single detector for differentially detecting a toxin such as toxin B from a highly virulent *C. difficile* strain (e.g., NAP 1) relative to the toxin from a less virulent *C. difficile* strain.
Figure 5:
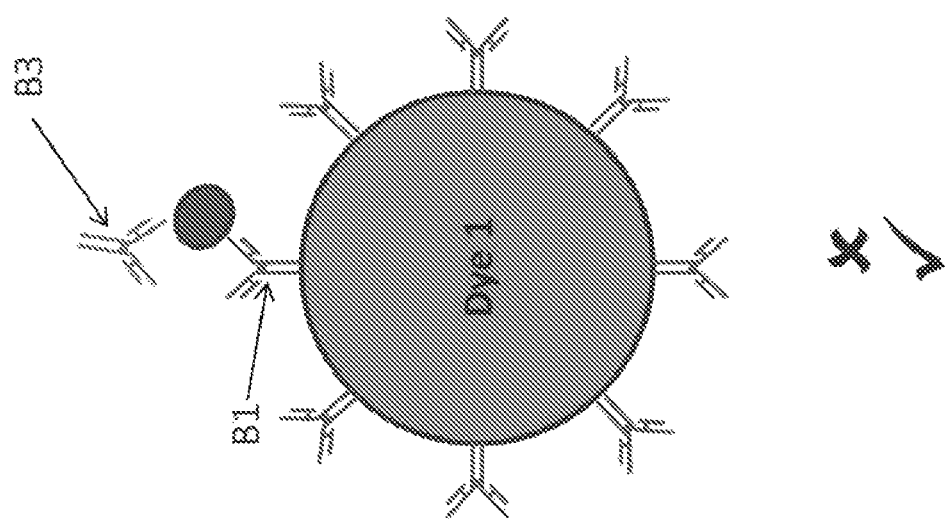
Figure 6:
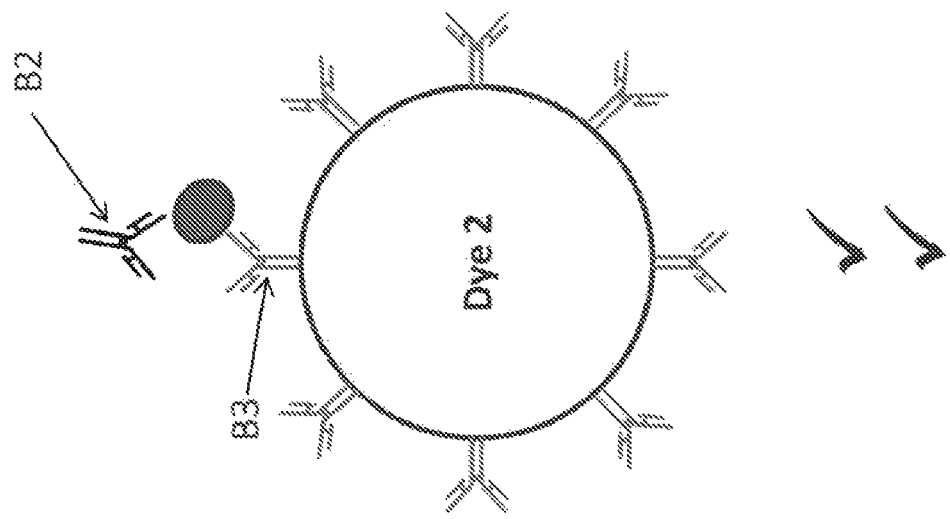
FIG. 6 is a schematic illustration showing a representative simplified assay with a single detector and capture switch for differentially detecting a toxin such as toxin B from a highly virulent *C. difficile* strain (e.g., NAP 1) relative to the toxin from a less virulent *C. difficile* strain.
Figure 6:
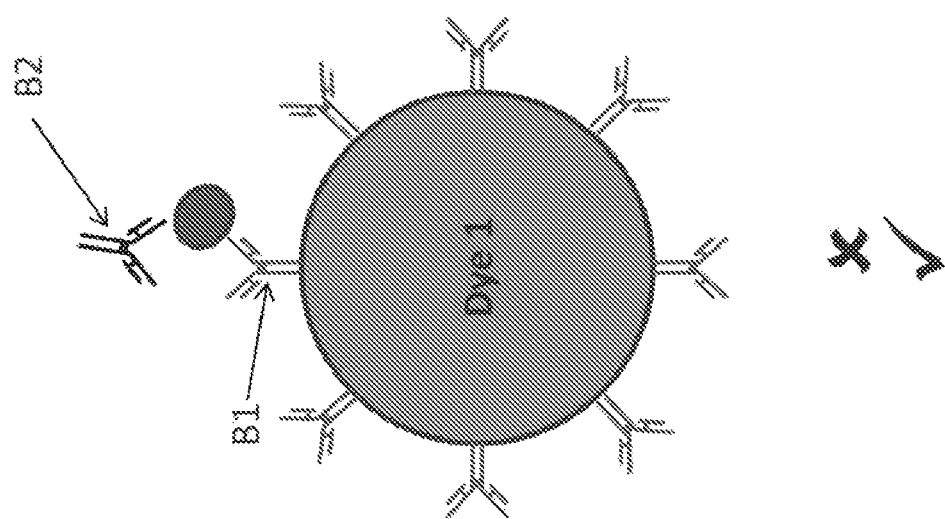

The differential detection method described herein that involves two immunoassays can be of any suitable format. In some instances, the differential detection method is a multiplex assay, in which different capture antibodies can be used in the first and second immunoassays. FIG. 4. In other instances, the differential detection method is a simplified assay with a single detector, in which the same antibody can be used as the capture antibody in both the first and second immunoassays. FIGS. 5 and 6. Preferably, in each immunoassay, an antibody that is capable of binding to a toxin (e.g., toxin B) of a broad spectrum of C. difficile strains, and the antibody that conjugates to a label (e.g., a dye) can be an antibody that differentially binds to the toxin (e.g., toxin B) of a highly virulent C. difficile strain as compared to the toxin of a less virulent C. difficile strain. In some examples, the labels (e.g., a dye) used in the first and second immunoassays are identical. In other examples, different labels are used in the first and second immunoassays.

Those of ordinary skill in the art will be aware of a variety of assay methods and systems that may be used in connection with the methods described herein. Generally, the methods employed have low limits of detection and/or limits of quantification as compared to bulk analysis techniques (e.g., ELISA methods). The use of assay methods that have low limits of detection and/or limits of quantification allows for correlations to be made between the various parameters discussed above and a method of treatment and/or diagnostic indication that may otherwise not be determinable and/or apparent.

The terms "limit of detection" (or LOD) and "limit of quantification" (or LOQ) are given their ordinary meaning in the art. The LOD refers to the lowest analyte concentration likely to be reliably distinguished from background noise and at which detection is feasible. The LOD as used herein is defined as three standard deviations (SD) above background noise. The LOQ refers to the lowest concentration at which the analyte can not only be reliably detected but at which some predefined goals for bias and imprecision are met. Generally, as is used herein, the LOQ refers to the lowest concentration above the LOD wherein the coefficient of variation (CV) of the measured concentrations is less than about 20%.

In some embodiments, an assay method employs a step of spatially segregating biomarker molecules into a plurality of locations to facilitate detection/quantification, such that each location comprises/contains either zero or one or more biomarker molecules. Additionally, in some embodiments, the locations may be configured in a manner such that each location can be individually addressed. In some embodiments, a measure of the concentration of biomarker molecules in a fluid sample may be determined by detecting biomarker molecules immobilized with respect to a binding surface having affinity for at least one type of biomarker molecule. In certain embodiments the binding surface may form (e.g., a surface of a well/reaction vessel on a substrate) or be contained within (e.g., a surface of a capture object, such as a bead, contained within a well) one of a plurality of locations (e.g., a plurality of wells/reaction vessels) on a substrate (e.g., plate, dish, chip, optical fiber end, etc). At least a portion of the locations may be addressed and a measure indicative of the number/percentage/fraction of the locations containing at least one biomarker molecule may be made. In some cases, based upon the number/percentage/fraction, a measure of the concentration of biomarker molecules in the fluid sample may be determined. The measure of the concentration of biomarker molecules in the fluid sample may be determined by a digital analysis method/system optionally employing Poisson distribution adjustment and/or based at least in part on a measured intensity of a signal, as will be known to those of ordinary skill in the art. In some cases, the assay methods and/or systems may be automated.

Additional details of exemplary, non-limiting assay methods which comprise one or more steps of spatially segregating biomarker molecules will now be described. In certain embodiments, a method for detection and/or quantifying biomarker molecules in a sample comprises immobilizing a plurality of biomarker molecules with respect to a plurality of capture objects (e.g., beads) that each include a binding surface having affinity for at least one type of biomarker. For example, the capture objects may comprise a plurality of beads comprising a plurality of capture components (e.g., an antibody as described herein). At least some of the capture objects may be spatially separated/segregated into a plurality of locations, and at least some of the locations may be addressed/interrogated (e.g., using an imaging system). A measure of the concentration of biomarker molecules in the fluid sample may be determined based on the information received when addressing the locations (e.g., using the information received from the imaging system and/or processed using a computer implemented control system). In some cases, a measure of the concentration may be based at least in part on the number of locations determined to contain a capture object that is or was associated with at least one biomarker molecule. In other cases and/or under differing conditions, a measure of the concentration may be based at least in part on an intensity level of at least one signal indicative of the presence of a plurality of biomarker molecules and/or capture objects associated with a biomarker molecule at one or more of the addressed locations.

In some embodiments, the number/percentage/fraction of locations containing a capture object but not containing a biomarker molecule may also be determined and/or the number/percentage/fraction of locations not containing any capture object may also be determined. In such embodiments, a measure of the concentration of biomarker molecules in the fluid sample may be based at least in part on the ratio of the number of locations determined to contain a capture object associated with a biomarker molecule to the total number of locations determined to contain a capture object not associated with a biomarker molecule, and/or a measure of the concentration of biomarker molecule in the fluid sample may be based at least in part on the ratio of the number of locations determined to contain a capture object associated with a biomarker molecule to the number of locations determined to not contain any capture objects, and/or a measure of the concentration of biomarker molecule in the fluid sample may be based at least in part on the ratio of the number of locations determined to contain a capture object associated with a biomarker molecule to the number of locations determined to contain a capture object. In yet other embodiments, a measure of the concentration of biomarker molecules in a fluid sample may be based at least in part on the ratio of the number of locations determined to contain a capture object and a biomarker molecule to the total number of locations addressed and/or analyzed.

In certain embodiments, at least some of the plurality of capture objects (e.g., at least some associated with at least one biomarker molecule) are spatially separated into a plurality of locations, for example, a plurality of reaction vessels in an array format. The plurality of reaction vessels may be formed in, on and/or of any suitable material, and in some cases, the reaction vessels can be sealed or may be formed upon the mating of a substrate with a sealing component, as discussed in more detail below. In certain embodiments, especially where quantization of the capture objects associated with at least one biomarker molecule is desired, the partitioning of the capture objects can be performed such that at least some (e.g., a statistically significant fraction; e.g., as described in WO 2011/109364, by Duffy et al., the relevant disclosures of which are incorporated by reference herein) of the reaction vessels comprise at least one or, in certain cases, only one capture object associated with at least one biomarker molecule and at least some (e.g., a statistically significant fraction) of the reaction vessels comprise an capture object not associated with any biomarker molecules. The capture objects associated with at least one biomarker molecule may be quantified in certain embodiments, thereby allowing for the detection and/or quantification of biomarker molecules in the fluid sample by techniques described in more detail herein.

An exemplary assay method may proceed as follows. A sample fluid containing or suspected of containing biomarker molecules is provided. An assay consumable comprising a plurality of assay sites is exposed to the sample fluid. In some cases, the biomarker molecules are provided in a manner (e.g., at a concentration) such that a statistically significant fraction of the assay sites contain a single biomarker molecule and a statistically significant fraction of the assay sites do not contain any biomarker molecules. The assay sites may optionally be exposed to a variety of reagents (e.g., using a reagent loader) and or rinsed. The assay sites may then optionally be sealed and imaged (see, for example, US 2012-0196774," by Fournier et al., the relevant disclosures of which are incorporated by reference herein.). The images are then analyzed (e.g., using a computer implemented control system) such that a measure of the concentration of the biomarker molecules in the fluid sample may be obtained, based at least in part, by determination of the number/fraction/percentage of assay sites which contain a biomarker molecule and/or the number/fraction/percentage of sites which do not contain any biomarkers molecules. In some cases, the biomarker molecules are provided in a manner (e.g., at a concentration) such that at least some assay sites comprise more than one biomarker molecule. In such embodiments, a measure of the concentration of biomarker molecules in the fluid sample may be obtained at least in part on an intensity level of at least one signal indicative of the presence of a plurality of biomarkers molecules at one or more of the assay sites In some cases, the methods optionally comprise exposing the fluid sample to a plurality of capture objects, for example, beads. At least some of the biomarker molecules are immobilized with respect to a bead. In some cases, the biomarker molecules are provided in a manner (e.g., at a concentration) such that a statistically significant fraction of the beads associate with a single biomarker molecule and a statistically significant fraction of the beads do not associate with any biomarker molecules. At least some of the plurality of beads (e.g., those associated with a single biomarker molecule or not associated with any biomarker molecules) may then be spatially separated/segregated into a plurality of assay sites (e.g., of an assay consumable). The assay sites may optionally be exposed to a variety of reagents and/or rinsed. At least some of the assay sites may then be addressed to determine the number of assay sites containing a biomarker molecule. In some cases, the number of assay sites containing a bead not associated with a biomarker molecule, the number of assay sites not containing a bead and/or the total number of assay sites addressed may also be determined. Such determination(s) may then be used to determine a measure of the concentration of biomarker molecules in the fluid sample. In some cases, more than one biomarker molecule may associate with a bead and/or more than one bead may be present in an assay site. In some cases, the plurality biomarker molecules may be exposed to at least one additional reaction component prior to, concurrent with, and/or following spatially separating at least some of the biomarker molecules into a plurality of locations.

The biomarker molecules (e.g., toxin A or toxin B of *C. difficile*) may be directly detected or indirectly detected. In the case of direct detection, a biomarker molecule may comprise a molecule or moiety that may be directly interrogated and/or detected (e.g., a fluorescent entity). In the case of indirect detection, an additional component is used for determining the presence of the biomarker molecule. For example, the biomarker molecules (e.g., optionally associated with a bead) may be exposed to at least one type of binding ligand. A "binding ligand," is any molecule, particle, or the like which specifically binds to or otherwise specifically associates with a biomarker molecule to aid in the detection of the biomarker molecule. In certain embodiments, a binding ligand may be adapted to be directly detected (e.g., the binding ligand comprises a detectable molecule or moiety) or may be adapted to be indirectly detected (e.g., including a component that can convert a precursor labeling agent into a labeling agent). A component of a binding ligand may be adapted to be directly detected in embodiments where the component comprises a measurable property (e.g., a fluorescence emission, a color, etc.). A component of a binding ligand may facilitate indirect detection, for example, by converting a precursor labeling agent into a labeling agent (e.g., an agent that is detected in an assay). A "precursor labeling agent" is any molecule, particle, or the like, that can be converted to a labeling agent upon exposure to a suitable converting agent (e.g., an enzymatic component). A "labeling agent" is any molecule, particle, or the like, that facilitates detection, by acting as the detected entity, using a chosen detection technique. In some embodiments, the binding ligand may comprise an enzymatic component (e.g., horseradish peroxidase, beta-galactosidase, alkaline phosphatase, etc.). A first type of binding ligand may or may not be used in conjunction with additional binding ligands (e.g., second type, etc.).

More than one type of binding may be employed in any given assay method, for example, a first type of binding ligand and a second type of binding ligand. In one example, the first type of binding ligand is able to associate with a first type of biomarker molecule and the second type of binding ligand is able to associate with the first binding ligand. In another example, both a first type of binding ligand and a second type of binding ligand may associate with the same or different epitopes of a single biomarker molecule, as described herein. In some embodiments, at least one binding ligand comprises an enzymatic component.

In some embodiments, a binding ligand and/or a biomarker may comprise an enzymatic component. The enzymatic component may convert a precursor labeling agent (e.g., an enzymatic substrate) into a labeling agent (e.g., a detectable product). A measure of the concentration of biomarker molecules in the fluid sample can then be determined based at least in part by determining the number of locations containing a labeling agent (e.g., by relating the number of locations containing a labeling agent to the number of locations containing a biomarker molecule (or number of capture objects associated with at least one biomarker molecule to total number of capture objects)). Non-limiting examples of enzymes or enzymatic components include horseradish peroxidase, beta-galactosidase, and alkaline phosphatase. Other non-limiting examples of systems or methods for detection include embodiments where nucleic acid precursors are replicated into multiple copies or converted to a nucleic acid that can be detected readily, such as the polymerase chain reaction (PCR), rolling circle amplification (RCA), ligation, Loop-Mediated Isothermal Amplification (LAMP), etc. Such systems and methods will be known to those of ordinary skill in the art, for example, as described in "DNA Amplification: Current Technologies and Applications," Vadim Demidov et al., 2004, the relevant disclosures of which are incorporated by reference herein.

Another exemplary embodiment of indirect detection is as follows. In some cases, the biomarker molecules may be exposed to a precursor labeling agent (e.g., an enzymatic substrate) and the enzymatic substrate may be converted to a detectable product (e.g., fluorescent molecule) upon exposure to a biomarker molecule.

The assay methods and systems may employ a variety of different components, steps, and/or other aspects that will be known and understood by those of ordinary skill in the art. For example, a method may further comprise determining at least one background signal determination (e.g., and further comprising subtracting the background signal from other determinations), wash steps, and the like. In some cases, the assays or systems may include the use of at least one binding ligand, as described herein. In some cases, the measure of the concentration of biomarker molecules in a fluid sample is based at least in part on comparison of a measured parameter to a calibration curve. In some instances, the calibration curve is formed at least in part by determination at least one calibration factor, as described above.

In certain embodiments, solubilized, or suspended precursor labeling agents may be employed, wherein the precursor labeling agents are converted to labeling agents which are insoluble in the liquid and/or which become immobilized within/near the location (e.g., within the reaction vessel in which the labeling agent is formed). Such precursor labeling agents and labeling agents and their use is described in US-2010-0075862, by Duffy et al., the relevant disclosures thereof are incorporated by reference herein.

Certain methods and systems suitable for performing any of the detection assays described herein are known in the art. See, e.g., US20070259448 (by Walt et al.); US20070259385 (by Walt et al.); US20070259381 (by Walt et al.); WO2009029073 (by Walt et al.); US20100075862 (by Duffy et al.); US201000754072 (by Duffy et al.); US20100075439 (by Duffy et al.); WO2010/039179 (by Duffy et al.); US20100075355 (by Duffy et al.); US20110212848 (by Duffy et al.); WO 2011/109364 (by Duffy et al.); WO 2011/109372 (by Duffy et al.); US20110212462 (by Duffy et al.); WO 2011/109379 (by Rissin et al.); US20110212537 (by Duffy et al.); US20120196774 (by Fournier et al.); US 2011-0245097 (by Rissin et al.). The relevant disclosures of each of those are incorporated by reference herein.

Detection of Both Toxin A and Toxin B

Another aspect of the present disclosure provides an ultrasensitive and quantitative assay method for diagnosing *C. difficile* infection, which involves detecting or quantifying both toxin A and toxin B. In some embodiments, the assay method includes two immunoassays, one for detecting toxin A of *C. difficile* and the other for detecting toxin B of *C. difficile*. Antibodies specific to toxin A or toxin B can be used in the two immunoassays. The anti-toxin A antibody can be an antibody that is capable of binding to toxin A of a broad spectrum of *C. difficile* strains, including highly virulent strains and less virulent strains. Alternatively or in addition, the anti-toxin B antibody can be an antibody that is capable of binding to toxin B of a broad spectrum of *C. difficile* strains, including highly virulent strains and less virulent strains. Such an anti-toxin A antibody or an anti-toxin B antibody may bind to an epitope common to toxin A or toxin B of the various strains, which can be identified by comparing the amino acid sequences of toxin A or toxin B as known in the art. Such an assay method would allow for detecting the presence of various *C. difficile* strains, regardless of their virulence levels.

The immunoassays can be of any format known in the art, e.g., those disclosed herein. In some examples, one or both of the immunoassays are Sandwich assays, which involve the use of two anti-toxin A antibodies and/or two anti-toxin B antibodies, one being a capture antibody and the other being a detection antibody. The capture antibody can be immobilized on a solid support, which can be a bead or a multi-well plate. The detection antibody can be conjugated to a label, e.g., those described herein. In a preferred example, the label is a catalyst, such as an enzyme, so that the detecting signal can be amplified.

In one example, both of the immunoassays for detecting toxin A and toxin B are digital ELISA assays as described herein. Such assays can be performed using systems and devices known in the art or disclosed herein.

In some cases, an assay method as described herein has a limit of detection of about 0.3 pg/mL (e.g., 0.4 pg/mL, 0.5 pg/mL, 0.8 pg/mL, 1 pg/mL, 5 pg/mL, or 10 pg/mL) for toxin A and about 1 pg/mL for toxin B (e.g., 1.2 pg/mL, 1.5 pg/mL, 1.8 pg/mL, 2 pg/mL, 5 pg/mL, 10 pg/mL, 15 pg/mL, 20 pg/mL, or 30 pg/mL).

Clinical Applications

Any one of the detection methods described herein, including the differential detection methods and the toxin A/toxin B detection method, can be applied in clinical settings for diagnosing *C. difficile* infection. To diagnose *C. difficile* in a subject having or suspected of having *C. difficile* infection, such as a human patient, a biological sample can be obtained from the subject. The biological sample can be a body fluid sample (e.g., blood or urine). Alternatively the biological sample can be a stool sample, which can be processed before applying a detection method as described herein.

In some embodiments, a biological sample can be analyzed by the method described herein to detect or quantify both toxin A and toxin B in the sample. Presence of toxin-producing *C. difficile* in the sample can be determined if the concentration of toxin A in the sample, the concentration of toxin B in the sample, or both, are above a cutoff value(s). For example, if the concentration of toxin B is higher than about 20 pg/ml as determined by a digital ELISA method described herein, it can be determined that the sample contains *C. difficile* cells producing toxin B. If the subject is diagnosed as infected by *C. difficile*, a suitable treatment can be determined for treating the subject. Also, since the level of toxin A and/or toxin B appears to correlate with disease severity, the results obtained from the detection method can be relied upon to predict disease course and/or treatment outcome. Detection of the presence and/or concentration of a toxin (e.g., toxin A or toxin B) has higher clinical specificity than detection of the organism per se. This is one of the advantages of the present method over detection methods known in the art, such as NAAT and culture-based methods.

In other embodiments, a biological sample can be analyzed by applying a differential detection assay as described herein to detect or quantify toxin B of either highly virulent *C. difficile* strains or toxin B of less virulent *C. difficile* strains. Based on the results, the presence of highly virulent *C. difficile* strains or less virulent *C. difficile* strains in the sample can be determined. If the subject is diagnosed as being infected by a highly virulent *C. difficile* strain, the subject can be treated by a suitable anti-*C. difficile* drug, e.g., an antibiotic such as metronidazole (Flagyl), Dificid (fidaxomicin), or vancomycin. Presence of highly virulent stains also provides clinically relevant prognostic information.

Any one of the detection assays described herein can be combined with one or more additional diagnosing approaches for better assessing *C. difficile* infection. For example, a subject (e.g., human patient) can be examined to determine one or more symptoms associated with *C. difficile* infection, e.g., diarrhea. In addition, a detection assay as described herein can be performed to detect the presence of toxin A, toxin B, or both in a biological sample from the subject (e.g., a stool sample). Further, a genetic assay (e.g., NAAT) can be performed to determine whether the subject is infected with a *C. difficile* strain that carries a gene encoding toxin A or toxin B. In some embodiments, the subject can be diagnosed as having *C. difficile* infection based on observation of a symptom associated with *C. difficile* infection (e.g., diarrhea), and the presence of toxin A, toxin B, or both in a biological sample of the subject. Such a diagnostic method may further comprise detecting the presence of a gene encoding toxin A or toxin B.

Kit for Performing the Detection Methods

Also within the scope of this disclosure are kits for use in performing any one of the detection assays described herein for diagnosing *C. difficile* infection.

Such a kit may comprise two pairs of anti-toxin B antibodies. The first pair includes two antibodies capable of binding to toxin B of a broad spectrum of *C. difficile* strains, including both highly virulent stains and less virulent stains. These two antibodies may bind to different epitopes of a toxin B polypeptide. The second pair includes one antibody that is capable of binding to toxin B of a broad spectrum of *C. difficile* strains (e.g., identical to one of the two antibodies in the first pair) and the other antibody differentially binds to toxin B of highly virulent *C. difficile* strains as relative to toxin B of less virulent *C. difficile* strains (e.g., specific to toxin B of a highly virulent *C. difficile* strain or specific to toxin B of a less virulent *C. difficile* strain) as described herein.

One of the two antibodies in the first pair, the second pair, or both may be immobilized on a solid support such as a bead or a multi-well plate. The other antibody may be conjugated with a label, e.g., an enzyme, a radioactive isotope, a DNA reporter, a fluorogenic reporter, or an electrochemiluminescent tag, all of which are well known in the art. In some examples, the antibody is conjugated with a catalyst such as an enzyme (e.g., those described herein) for signal amplification. Alternatively, this antibody may be conjugated with a member of a receptor/ligand pair and the kit may further comprise a conjugate comprising the other member of the receptor/ligand pair and any of the labels described herein (e.g., an enzyme). In one example, the antibody is labeled with biotin and the kit further comprises a streptavidin-enzyme conjugate.

In another embodiment, the kit may comprise two pairs of antibodies, the first pair including two antibodies binding to toxin B and the second pair including antibodies binding to toxin A. Antibodies of the first pair may be capable of binding to toxin B of a broad spectrum of *C. difficile* strains, including both highly virulent and less virulent strains. Alternatively or in addition, antibodies of the second pair may be capable of binding to toxin A of a broad spectrum of *C. difficile* strains, including both highly virulent and less virulent strains. One antibody of the first pair, the second pair, or both can be immobilized on a solid support and the other antibody may be conjugated with a label as described herein.

Any of the kits described here may further comprise one or more components for performing the detection assays (e.g., immunoassays). For example, when an enzyme is used as the label, a substrate of the enzyme can be included in the kit. Further, the kit may also comprise an instruction manual providing guidance for using the kit to perform any one of the detection assay provided herein, such as any one of the differential detection methods by, e.g., digital ELISA, or any one of the methods for detecting both toxin A and toxin B of *C. difficile* by, e.g., digital ELISA.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Differential Immunodetection of Toxin B of Highly Virulent *C. difficile* BI/NAP-1/027

Methods
Conventional Bead-Based ELISA
Mouse monoclonal antibodies against toxin B (B1, B2, and B3) were provided by bioMerieux (Lyon, France). Paramagnetic beads ($5 \times 10^6$/ml) coated in capture antibodies were incubated with culture filtrates (CF; see Example 2 below) in the wells of a microtiter plate for 2 h at room temperature. Captured toxin proteins were labeled with a biotinylated detection antibody (0.1 µg/ml) and an enzyme conjugate (0.5 nM). Following washes, enzyme substrate was added to the microtiter plate wells, and fluorescent signals were measured using a Tecan plate reader.

Digital ELISA
Details of the Simoa technology have been described previously [Rissin, D. M. et al., *Nat Biotechnol*, 28(6): p. 595-9 (2010); Rissin, D. M. et al., *Anal Chem*, 83(6): p. 2279-85 (2011)], and assays were performed on the Simoa HD-1 Analyzer (Quanterix Corporation). Kan et al., *Lab Chip*, 2011. Briefly, paramagnetic beads coated in capture antibodies were incubated with stool samples after dilution and filtration; captured toxin proteins were labeled with a biotinylated detection antibody and an enzyme conjugate (streptavidin-beta-galactosidase). Following the addition of an enzyme substrate, beads were loaded into arrays of femtoliter-sized wells for isolation and detection of bound molecules. Digital ELISAs were developed with two separate pairs of antibodies (B1 capture/B2 detector, and B2 capture/B3 detector). Signals from the digital ELISAs were calibrated by spiking known concentrations of purified native toxin B (prepared from strain VPI using established methods) into either buffer or toxin-negative stool samples.

Specimen Collection and Testing
A panel of REA-typed clinical strains were each cultured in chopped meat broth for 24 hours. Culture filtrates (CF) were prepared by 3000×g centrifugation to obtain supernatant, followed by passage through 0.2 µm syringe filter. CF were tested by conventional ELISA as described above.

In all, 149 clinical stool specimens (each <72 hours old) that had been tested for toxigenic *C. difficile* by NAAT (Meridian Illumigene) were aliquoted and frozen at −80° C.; this study was approved by the BIDMC IRB. Aliquots were subsequently tested by digital ELISA (Quanterix, Lexington, Mass.) and by toxigenic culture (TC) (Gerding laboratory, Hines VA Hospital, IL) [Tenover, F. C. et al., *J Clin Microbiol*, 49(5): p. 1831-7 (2011)]. All *C. difficile* isolates recovered from TC were typed by restriction endonuclease analysis (REA; Gerding laboratory) [Clabots, C. R. et al., *J Clin Microbiol*, 31(7): p. 1870-5 (1993)].

Results
Detection of Toxin B Produced In Vitro by Divergent Clinical Isolates

The ability of the antibody pairs to detect native toxin B of CF prepared from a panel of 12 clinical *C. difficile* isolates representing major strains in circulation as well as key control strains was evaluated first (FIG. 1A). The high abundance of toxin in vitro allowed the use of conventional bead-based ELISA for these experiments. Relative amounts of toxin B in each sample as measured with each antibody pair, expressed in relative fluorescent units (RFU), were compared. Signal below the analytical limit of detection (defined as 3 SD above assay background, RFU=157) for each assay was interpreted as "not detected" (ND); the signal was considered saturated at 50,000 RFU. Two toxin B assays as described above differentially detected toxin B as follows: the B1/B2 pair (B1 capture, B2 detection) detected toxin B of all B-producing strains except all three BI/NAP-1/027 strains (CF10, 11, and 12; FIG. 1A), while the B2/B3 pair (B2 capture, B3 detection) detected toxin B of all B-producing strains (FIG. 1A). For detection of toxin B of the BK1/078 strain (CF13, FIG. 1A), the signal detected using the B2/B3 pair was ~21-fold more than that using the B1/B2 pair.

To confirm that the differential toxin detection observed was specifically due to differential binding of the B1 vs. B3 antibodies to toxin B, the CFs were retested via conventional ELISA using the B2 antibody as the capture antibody in combination with B1 vs. B3 as the detecting antibody, and obtained exactly the same results.

Detection of Toxin B Produced In Vivo by Divergent Clinical Isolates

Figure 1B:
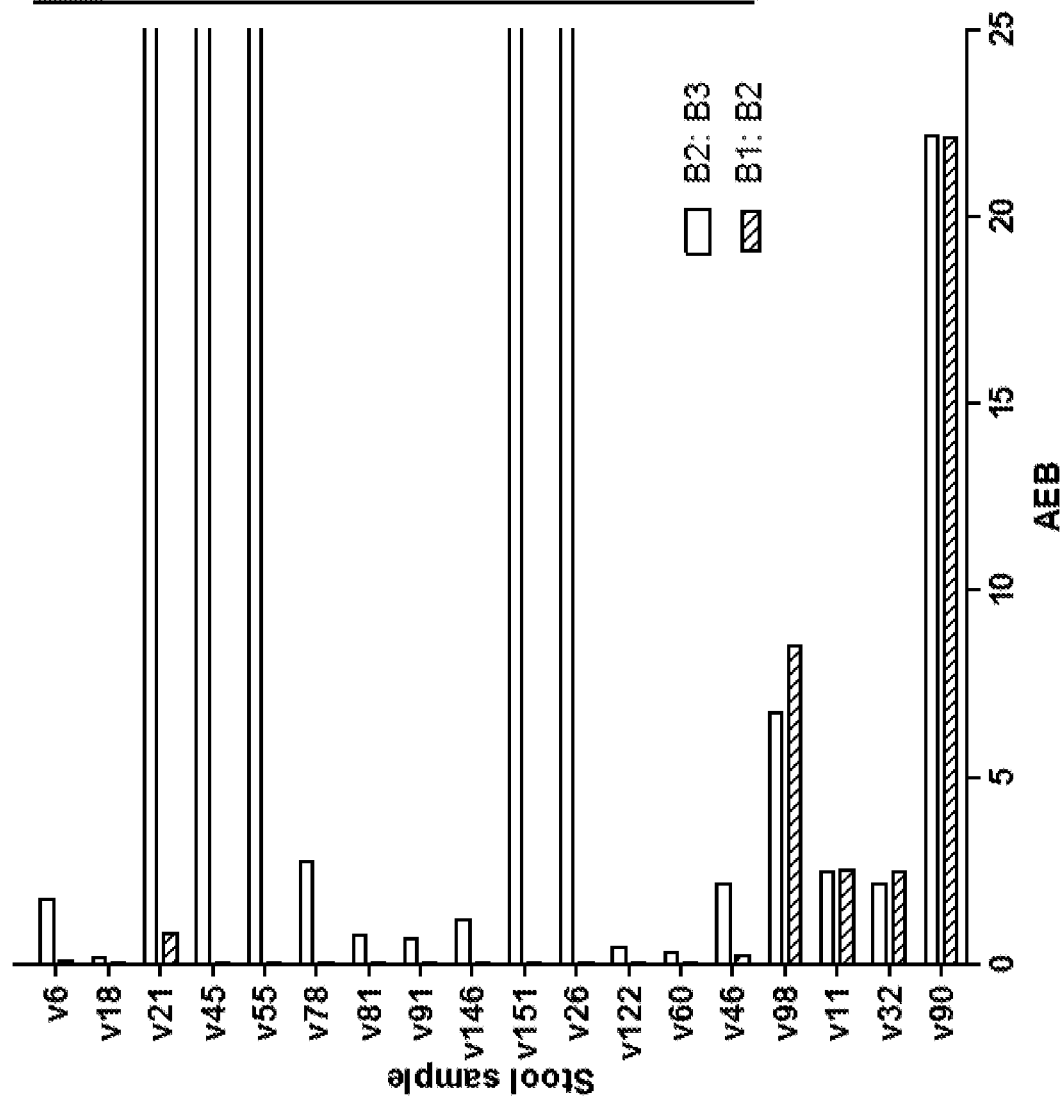
FIG. 1B is a chart showing the comparison of toxin B levels in clinical stool samples, which in toxigenic culture, yielded isolates with REA types shown (table inset), as measured by digital ELISA using the B2/B3 antibody pair (white bars) vs the B1/B2 antibody pair (hatched bars).

Two digital ELISA assays were used to directly detect toxin B in clinical stool samples, and the results of toxin detection were correlated with the results of REA typing of the corresponding C. difficile isolates from TC. The lower abundance of toxin in in vivo samples necessitated the use of a single molecule immunoassay. Similar to results obtained with CF, differential detection of toxin B (by the two digital ELISAs) was observed in stool samples from which BI/NAP-1/027 isolates were recovered. Specifically, for all stool samples from which BI/NAP-1/027 isolates were recovered (n=10), levels of toxin B as measured by the B2/B3 digital ELISA were >20-fold higher than levels of toxin B as measured by the B1/B2 pair (FIG. 1B). Differential toxin detection was also observed in three other stool samples, which yielded C. difficile isolates with the following characteristics: two (sample IDs v26 and v122) were from separate but undefined REA groups, and the third (sample ID v60) was a member of the REA Group AF. Notably, Group AF includes PCR ribotype 244, a strain which has been shown to have genetic similarity to BI/NAP-1/027 strains and to similarly be associated with more severe disease [Lim, et al., Clin Infect Dis, (2014)]. For all other stool samples yielding toxigenic isolates (n=53), the ratio of the toxin B level as measured by the B2/B3 assay to that measured by the B1/B2 assay ranged from 0.1-12.3 (mean of 1.8); representative examples are presented in FIG. 1B (v46, v98, v11, v32, and v90).

Conclusions

In this study, two monoclonal antibodies were found to exhibit differential binding to C. difficile toxin B of highly virulent strains (BI/NAP-1/027 and BK/078) compared to other strain types. This indicates antigenic similarities between toxin B of BI/NAP-1/027 and BK/078 strains that are not present in toxin B of other strain types. This serendipitous observation was exploited to develop a simple, quantitative, and sensitive immunoassay (digital ELISA, based on Simoa technology) to differentially detect toxin B of these highly virulent strains. The differentiating capacity of the digital ELISA is important for two reasons. First, while toxins from different strain types have been hypothesized to be antigenically distinct, this has not been definitively demonstrated for the BI/NAP-1/027, BK/078, or AF group/ribotype 244 strains (nor for most toxinotypes [Rupnik, FEMS Microbiol Rev, 32(3): p. 541-55 (2008)]). Second, because the digital ELISAs can differentially distinguish toxins from these highly virulent strains in clinical stool samples, the digital ELISA represents a sensitive stool immunoassay that can simultaneously identify the presence of toxigenic C. difficile, confirm in vivo toxin production, quantify stool toxin concentrations, and report the presence of highly virulent strains (particularly BI/NAP-1/027), thereby providing clinically relevant prognostic information.

Example 2: Preclinical and Clinical Validation of Digital ELISAs for Ultrasensitive Detection and Quantification of C. difficile Toxins A and B in Stool Described herein is the development and validation of ultrasensitive and quantitative "digital ELISA" assays for toxins A and B based on single molecule array (Simoa) technology [32, 33]). Simoa technology is based on the high efficiency capture and labeling of single protein molecules on paramagnetic beads, and their detection in arrays of femtoliter-sized wells [32, 33]. The ability to isolate and detect single protein molecules leads to dramatic improvements in sensitivity such that fg/mL concentrations of proteins can be detected, typically 1000-fold more sensitive than conventional ELISA. Digital ELISAs have been shown to be highly robust and reproducible for detection of low levels of proteins in highly complex matrices including cell culture supernatant, serum, plasma, and cerebral spinal fluid (CSF) [32-37]. The assays described herein represent the first application of Simoa to measurement of proteins in stool specimens. We submit that our new assays may provide clinical sensitivity equal to that of NAAT and TC, with higher clinical specificity, and thus offer the potential for a new approach to the diagnosis and management of CDI.

This study relates to ultrasensitive "digital ELISA" assays for toxins A and B using single molecule array technology and validated using a) culture filtrates from a panel of clinical C. difficile isolates and b) 149 adult stool specimens already tested by NAAT per clinical routine. This rapid, simple tool allows diagnosis of CDI with both high analytical sensitivity and high clinical specificity.

Materials and Methods

Antibody Conjugation and Biotinylation

Antibody-coated capture beads were prepared as follows: paramagnetic particles functionalized with COOH groups (Agilent) were washed three times with 1×PBS+1% Tween 20, followed by two washes with 50 mM MES (2-(N-morpholino)ethanesulfonic acid), pH 6. Beads were subsequently activated with 0.5 mg/ml freshly prepared EDAC (1-Ethyl-3-(3-dimethylaminopropyl)carbodiimide) in cold 50 mM MES buffer (pH 6.0) for 30 minutes at room temperature. After activation, beads were immediately washed with cold MES buffer (pH 6.0), and incubated with 0.5 mg/ml of antibody diluted in MES buffer (pH 6.0) for 2 hours at room temperature for conjugation. Antibody-coated beads were then washed twice with 1×PBS+1% Tween 20 and blocked with 1×PBS+1% BSA for 30 minutes. After blocking, beads were washed and stored in 50 mM Tris buffer with 1% BSA, pH 7.8 at 4° C. for future use. Detection antibody was biotinylated in-house using EZ-link NHS-PEG$_4$-Biotin (Thermo Scientific) following the manufacturer's instructions. Briefly, antibody was first buffer-exchanged into phosphate buffer and then reacted with NHS-PEG$_4$-Biotin at optimized concentrations for 30 minutes. After biotinylation, antibody was purified to remove excess free biotin using centrifuge filters and stored at 4° C. for future use.

Conventional ELISA

Conventional plate- and bead-based ELISA were used to screen antibodies for assay development and to test culture filtrates (CF). We ultimately selected one pair of monoclonal antibodies against toxin A (Meridian Life Sciences, Memphis, Tenn.) and another pair against toxin B (bioMerieux, Lyon, France). For bead-based ELISA, paramagnetic beads (5×10$^6$/ml) coated in capture antibodies were incubated with calibration buffer containing purified native toxins A or B (prepared from strain VPI10463 in C.P.K's laboratory using established methods, [38]) or CF in the wells of a microtiter plate for 2 h at room temperature. The calibration buffer (pH 7.4) contains 50 mM Tris-HCL, 150 mM NaCl, 0.5% BSA, 0.5% new born half serum (NBCS), 0.1% Tween 20, and 0.15% Proclin 300. Captured toxin proteins were labeled with a biotinylated detection antibody (0.1 µg/ml) and an enzyme conjugate (streptavidin-beta-galactosidase, 0.5 nM). Following washes, enzyme substrate was added to the microtiter plate wells, and fluorescent signals were measured using a Tecan plate reader.

Simoa Assays (Digital ELISAs)

Frozen aliquots of stool specimens were completely thawed at room temperature and mixed thoroughly either by vortexing or using a wooden applicator stick. Stool samples were then diluted and filtered to remove particulates before testing by digital ELISA.

Details of the Simoa technology used to develop and perform digital ELISA have been described previously [32, 33]. Antibody-coated capture beads and biotinylated detection antibodies were prepared using standard methods [32, 33]). Digital ELISAs were performed on the Simoa HD-1 Analyzer (Quanterix Corporation) [39] by automating the following steps. Capture beads ($2.5 \times 10^6$/ml, for both toxin A and B assays) were incubated with diluted stool samples for 15 min at 23° C. Beads were washed three times with 5x PBS+0.1% Tween 20. Captured toxin proteins were labeled with a biotinylated detection antibody (0.4 µg/mL for the A assay, 0.2 µg/mL for the B assay) and an enzyme conjugate (streptavidin-beta-galactosidase, 250 pM). Following addition of enzyme substrate, beads were loaded into arrays of femtoliter-sized wells for isolation and detection of bound molecules. Total assay time was 69 min.

Simoa signals were quantified as average enzymes per bead, or AEB [33]. Signals from the digital ELISAs were calibrated by spiking a series of known concentrations of purified native toxin A or B (prepared as previously described [38]) into either buffer or NAAT-negative stool samples processed as described above. Calibration curves were used to calculate toxin concentrations (pg/mL) in stool specimens. For each digital ELISA, all calibrators and samples were assayed in triplicate, and average AEB, SD, and CV % were calculated for measured toxin concentrations.

To evaluate assay accuracy, NAAT-negative stool samples were spiked (after dilution) with or without a known concentration of purified native toxin A or B, processed as described above, and tested by digital ELISA. Recovery of spiked toxins was calculated as follows: % recovery=(measured concentration in spiked stool−measured concentration in non-spiked stool)/expected concentration of spiked toxins).

For each digital ELISA, all calibrators and samples were assayed in triplicate, and average AEB, SD, and CV % were calculated as well as for measured toxin concentrations. To evaluate assay accuracy, NAAT-negative stool samples were spiked (after dilution) with or without a known concentration of purified native toxin A or B, centrifuged and filtered as described above, and tested by digital ELISA. Recovery of spiked toxins was calculated as follows: % recovery= (measured concentration in spiked stool−measured concentration in non-spiked stool)/expected concentration of spiked toxins).

Interfering Factor Analysis

A panel of potential interfering substances was evaluated to determine the effect of their presence in stool specimens on detection of toxin A or B using digital ELISA. Briefly, each of the potential interferents was individually spiked into diluted stool samples at targeted concentrations. These stool samples were then processed and concentrations of toxin A or B were measured and compared to controls without added interferent. The tested substances included (concentrations noted are maximum final concentrations tested) vancomycin (100 mg/mL), metronidazole (40 mg/mL), loperamide HCl, salicylate, bismuth subsalicylate, Imodium (tablets or liquid), pepto-bismol (tablets or liquid), barium sulfate, and 50% (v/v) whole blood.

Stool Sample Processing

Frozen aliquots of stool specimens were completely thawed at room temperature and mixed thoroughly either by vortexing or using a wooden applicator stick. Stool samples were then diluted 1:20 in sample diluent (50 mM Tris-HCl, 150 mM NaCl, 0.5% NBCS, 0.1% Tween 20, and 0.15% Proclin 300, pH 7.4) as follows: 3.8 mL of sample diluent was first added to a graduated centrifuge tube. For liquid stools, 200 µL sample was added to the diluent using a disposable transfer pipet; for semi-solid or solid stools, the specimen was carefully transferred (using a plastic disposable spatula) into the diluent until the level of liquid reached 4 mL. Diluted stool samples were then vortexed thoroughly and centrifuged at 9,500 g for 15 minutes. Supernatants were filtered using a 0.45 µm vacuum filter (EMD Millipore) and then assayed by digital ELISA.

An alternative sample diluent that contained more concentrated NBCS (50 mM Tris-HCl, 150 mM NaCl, 25% NBCS, 0.1% Tween 20, and 0.15% Proclin 300, pH 7.4) was applied to some (approximately 6%) stool samples to prevent bead aggregation during toxin capture. In such cases, a corresponding alternative calibration buffer (50 mM Tris-HCl, 150 mM NaCl, 0.5% BSA, 25% NBCS, 0.1% Tween 20, and 0.15% Proclin 300, pH 7.4) was used to generate calibration curves for determination of toxin concentrations in these stool samples.

Sample Collection and Testing (i) Culture Filtrates

A panel of clinical strains previously typed by restriction endonuclease analysis (REA) (provided by D.N.G.) were each cultured in chopped meat broth for 24 hours. CF were prepared by 3000×g centrifugation to obtain supernatant, followed by passage through an 0.2 µm syringe filter. CF were tested by conventional bead-based ELISA as described above.

(ii) Clinical Stool Specimens

Clinical stool specimens (each <72 hours old) that had been tested for toxigenic *C. difficile* by NAAT (Meridian Illumigene) were aliquoted and frozen at −80° C.; this study was approved by the BIDMC IRB. 52 samples (11 NAAT-positive, 41 NAAT-negative) were used for assay development, and 149 additional samples (65 NAAT-positive, 84 NAAT-negative) were collected for assay validation. Separate aliquots of each validation specimen were subsequently thawed and tested by digital ELISA, cytotoxicity assay, and toxigenic culture (TC). Relevant clinical and laboratory data corresponding to each sample was collected by chart review. The presence or absence of diarrhea as documented at the time of sample collection was determined using the following definition: three or more unformed bowel movements during any 24 hour period during the 48 hours before the time of stool collection, OR diarrhea specifically mentioned in MD/RN progress notes as being present in the 48 hours before stool collection.

(iii) Cytotoxicity Assay

Cytotoxicity assays were performed using standard methods [25] using stool samples diluted 1:100 in PBS, added to NIH 3T3 fibroblast cell monolayers and incubated for 24 h. A positive result required a typical cell rounding effect in >50% of cells that was inhibited using specific anti-serum to toxin A and B.

(iv) Toxigenic Culture (TC)

C. difficile (CD) culture was performed using standard, well-established methods [40] in D.N.G.'s laboratory. Stool samples were directly inoculated onto selective TCCFA plates and streaked for isolation. If initial TCCFA culture failed to yield colonies with characteristic CD morphology, an alcohol shock protocol was performed on the stool sample to enhance recovery of CD spores. All C. difficile isolates were evaluated for their ability to produce toxin in vitro by culturing in BHI media for 48-72 hours and testing supernatants in the Bartel's cell cytotoxicity assay (MarDx Diagnostics, Carlsbad, Calif.). Samples that yielded a C. difficile isolate that did not produce toxin were scored as TC negative. All C. difficile isolates recovered from CD culture were REA typed in D.N.G.'s laboratory using established methods [41, 42].

Results

Digital ELISA Development and Limit of Detection (LOD) in Buffer

A panel of antibodies were screened from commercial and academic sources by plate- and bead-based ELISA to find pairs that detected purified native toxin A or toxin B with highest analytical sensitivity and specificity (optimal signal/background). One pair of monoclonal antibodies were ultimately selected for each toxin assay (see Methods above; B2 and B3 disclosed in Example 1). As part of the screening process, culture filtrates (CF) prepared (Methods) from a panel of 12 clinical C. difficile isolates representing the major strains in circulation were also screened. It was observed that toxin A and B antibody pairs were able to detect their respective toxins in CF from all toxin-A and toxin B-producing strains in the panel. See Table 3 below.

TABLE 3

Detection of C. difficile Toxins A and B by Conventional Bead-Based ELISA in Culture Filtrates Prepared from a Panel of C. difficile Isolates.

| Culture filtrate | REA Type/strain information | Expected toxin production | Toxin A detection by bead-based ELISA | Toxin B detection by bead-based ELISA |
|---|---|---|---|---|
| CF1 | B1 | A+/B+ | + | + |
| CF2 | J9 | A+/B+ | + | + |
| CF3 | K14 | A+/B+ | + | + |
| CF4 | Y2 | A+/B+ | + | + |
| CF5 | CF2 | A−/B+ | ND | + |
| CF6 | ATCC BAA-1801 | NONE | ND | ND |
| CF7 | Medium | NONE | ND | ND |
| CF8 | VPI | A+/B+ | + | + |
| CF9 | R23 | sequenced A+B+ strain | + | + |
| CF10 | BI1 (historic NAP1) | A+/B+/binary+ | + | + |
| CF11 | BI6 (epidemic NAP1) | A+/B+/binary+ | + | + |
| CF12 | BI17 (epidemic NAP1) | A+/B+/binary+ | + | + |
| CF13 | BK1 (ribotype 078) | A+/B+/binary+ | + | + |

CF, culture filtrate; REA, Restriction Endonuclease Analysis; ND, not detected.

Figure 3:
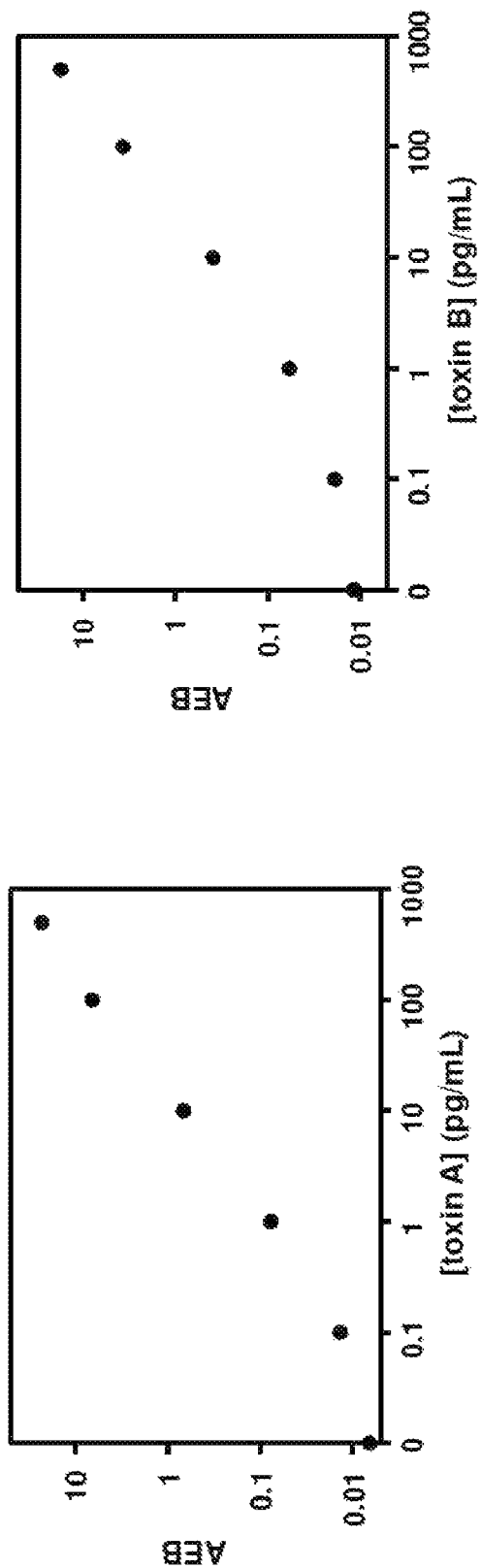
FIG. 3 is a diagram showing representative calibration curves for both toxin A and B assays. The LOD, defined as a concentration corresponding to the AEB from zero calibrator plus 3 SD, was 0.028 pg/ml for toxin A and 0.061 pg/ml for toxin B from the presented curves respectively, using a 10% CV for zero calibrator.

After optimization of the digital ELISAs, the typical LOD for native toxin spiked into calibration buffer was 0.028 pg/mL for the toxin A assay and 0.061 pg/mL for the toxin B assay (CVs ranged from 1-13%). See FIG. 3.

LOD in Stool

To measure LOD in stool, native, purified toxins A and B were spiked into clinical stool samples that had tested negative by NAAT (Meridian Illumigene) during routine clinical testing. Stool samples were diluted prior to spiking and then processed as described (Methods). LOD in stool was defined as an interpolated concentration corresponding to an average AEB from NAAT-negative stools plus 3 SD, and corrected for the dilution factor. Our assays detected native toxins in stool with LODs of 0.45 pg/mL (toxin A) and 1.50 pg/mL (toxin B), respectively. % recovery ranged from 50-125% (average 84%). The mean % CV of Simoa signal (AEB) was 8%; this imprecision translated into a mean imprecision of 15% in measured toxin concentrations for all stool specimens analyzed during this study, including those close to the LOD that have intrinsically higher imprecision. Of note, in ~6% of samples we observed aggregation of the paramagnetic beads (after incubation in the stool samples) that prevented measurement using Simoa. This limitation was overcome by using a modified dilution buffer for those samples that caused aggregation.

Interfering Factors

A panel of potential interferents [at concentrations at or above those tested for commercial EIAs (e.g. [43, 44])] was tested in our assay (Methods). There was no evidence of interference from supraphysiologic levels of vancomycin, metronidazole, loperamide HCl, salicylate, bismuth subsalicylate, Imodium (tablets or liquid), pepto-bismol (tablets or liquid), or barium sulfate, nor from 50% (v/v) whole blood.

Clinical Validation 149 clinical specimens (<72 hours old) that had tested either positive (n=65) or negative (n=84) by NAAT (Meridian Illumigene) during routine clinical testing were tested with the two digital ELISAs (each run in triplicate and averaged), cytotoxicity assay, and TC (latter followed by REA typing of all C. difficile isolates).

A clinical cutoff for positive for each digital ELISA was calculated by averaging the Simoa signal for "true negative" stool samples (n=80; negative by NAAT, TC, and cytotoxicity assay; FIGS. 2A and B), plus 3 standard deviations (SD) of that mean. One of the 80 "true negative" samples was excluded from the calculation of the cutoff because it was an extreme outlier on the toxin A assay (FIG. 2A, marked with arrow) and substantially distorted the mean for that assay. Using the remaining 79 true negatives, the calculated cutoff for positive was 29.4 pg/mL for the toxin A assay and 23.3 pg/mL for the toxin B assay; with these cutoffs, the toxin A and B digital ELISA specificities in the true negative group were 96% and 98%, respectively.

Figure 2B:
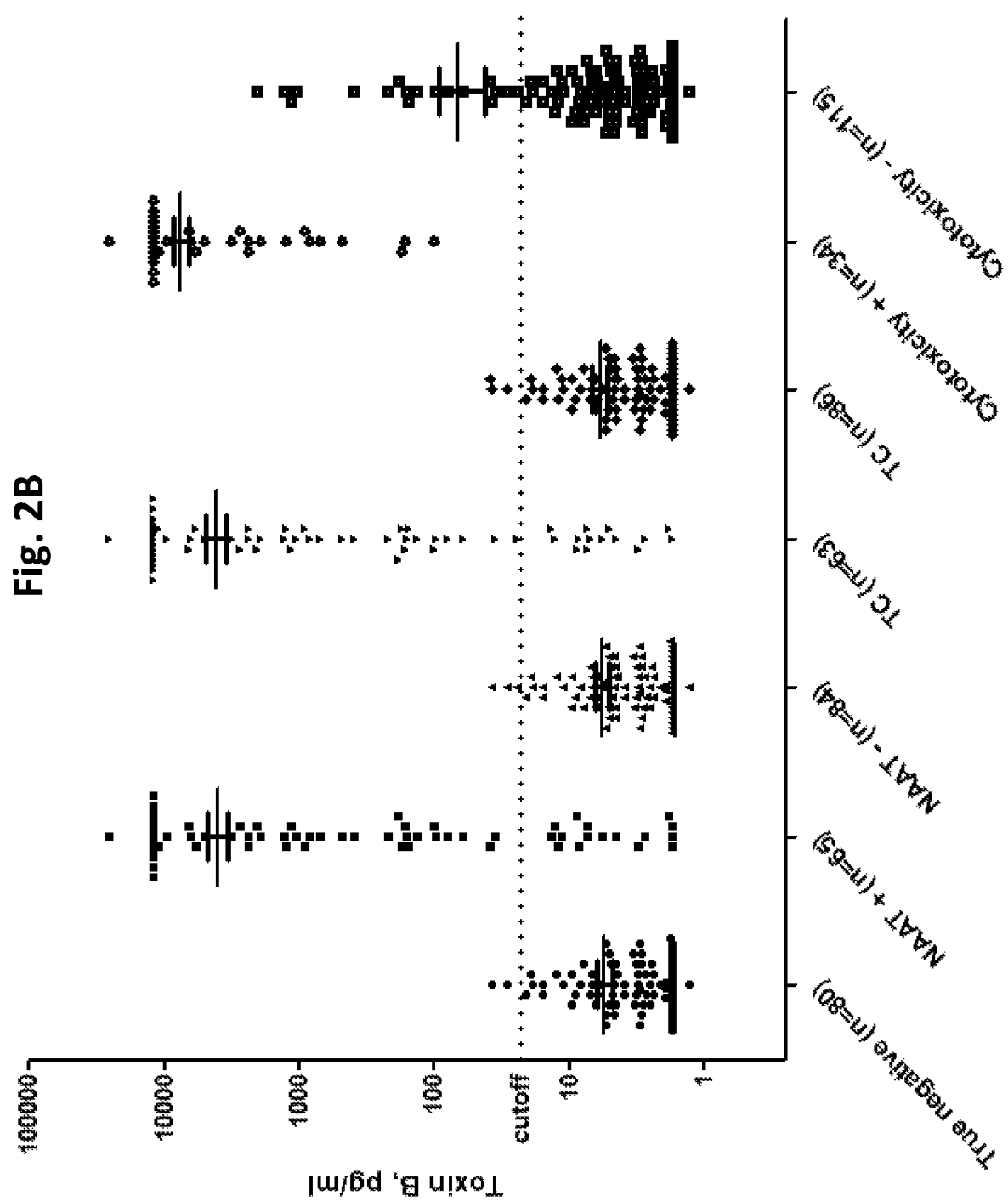
FIG. 2B is a graph showing the digital ELISA results for groups of samples testing positive vs. negative with other assays for toxin B. Mean signals in each group are indicated by horizontal lines. The calculated clinical cutoffs for each digital ELISA (23.3 pg/mL for the toxin B assay) are shown as dotted lines spanning each figure. NAAT, nucleic acid amplification testing; TC, toxigenic culture.

Plots of A and B digital ELISA results for groups of samples testing positive vs negative on other assays (i.e. NAAT+ vs NAAT−, TC+ vs TC−, and cytotoxicity+ vs cytotoxicity−) are shown in FIGS. 2A and B; mean signals in each group are indicated by horizontal lines, and the calculated cutoffs for each digital ELISA are shown as dotted lines spanning the entire figure. As expected, for the toxin B digital ELISA, 16/65 (25%) samples that were positive by NAAT and 14/63 (22%) samples which were positive by TC were negative by the toxin B digital ELISA, consistent with the presence of organism (but minimal or no toxin) in those samples (FIG. 2B). In contrast, 34/34 (100%) samples positive by cytotoxicity assay were positive by the toxin B digital ELISA.

As expected based on LODs, we noted some overlap between toxin B digital ELISA signals in cytotoxicity+ vs cytotoxicity− samples in the range of ~102-2078 pg/mL (FIG. 1B), indicating that in this range the cytotoxicity assay was variably sensitive. Results from the toxin A digital ELISA (FIG. 2A) revealed four samples for which cytotoxicity assay and TC were positive but toxin A digital ELISA was negative. REA typing of isolates obtained from TC confirmed that all four isolates were REA type CF, a group of isolates that produce toxin B but not toxin A. TC and cytotoxicity assay were used as alternative laboratory gold standards for calculations of digital ELISA sensitivity and specificity (Table 2); for comparison, we also calculated sensitivity and specificity of each digital ELISA vs NAAT (Table 4). Toxin concentrations (pg/mL) measured by digital ELISA spanned a >4 log dynamic range (FIG. 2A,B).

TABLE 4

Sensitivity and Specificity of the Toxin A and B Digital ELISAs as Compared to Three Alternative Reference Standards by Nucleic Acid Amplification Testing (NAAT).

| | Sensitivity vs. reference standard shown | | | Specificity vs. reference standard shown | | |
|---|---|---|---|---|---|---|
| | Toxigenic culture (%) | Cytotoxicity assay (%) | NAAT (%) | Toxigenic culture (%) | Cytotoxicity assay (%) | NAAT (%) |
| Toxin A digital ELISA | 75 | 88 | 71 | 95 | 84 | 94 |
| Toxin B digital ELISA | 78 | 100 | 75 | 97 | 87 | 96 |

Correlation of Toxin Detection with Disease and Disease Severity

Among the 73 patients whose stool tested positive by any of the assays used (toxin A and B digital ELISAs, NAAT, TC, or cytotoxicity assay), there were 8 subjects who had a severe outcome potentially attributable to CDI, as defined by death, ICU admission, or colectomy within 40 days of stool testing. For those 8 subjects, detailed chart review (by clinicians blinded to stool assay results, other than NAAT) indicated that 5/8 severe outcomes were likely attributable to CDI. Mean toxin levels (toxin [A], toxin [B], or toxin [A+B]) in the 5 subjects with CDI-attributable severe outcomes were higher (1.7-fold, 1.5-fold, and 1.6-fold, respectively) than mean toxin levels in the 68 subjects without CDI-attributable severe outcomes, though this was not statistically significant (p=0.099, 0.182, and 0.084, respectively).

In sum, the digital ELISAs detected toxins A and B in stool with limits of detection of 0.45 and 1.5 pg/mL respectively, quantified toxins across a 4-log dynamic range, and detected toxins from all major clinical strains studied. Using specimens negative by cytotoxicity assay/TC/NAAT, clinical cutoffs were set at 29.4 pg/mL (A) and 23.3 pg/mL (B); resulting clinical specificities were 96% and 98%, respectively. The toxin B digital ELISA was 100% sensitive vs cytotoxicity assay. 25% and 22% of samples positive by NAAT and TC, respectively, were negative by the toxin B digital ELISA, consistent with the presence of organism (but minimal or no toxin) in those samples. Mean toxin levels by digital ELISA were 1.5-1.7-fold higher in patients with CDI-attributable severe outcomes, vs. those without.

Discussions

Within the complex and rapidly shifting *C. difficile* diagnostic landscape, one major theme is emerging: that detection of toxin, rather than of bacteria capable of producing that toxin, is the key to accurate diagnosis of CDI [2, 15, 16, 46]. Qualitative enzyme immunoassays (EIAs) that detect *C. difficile* toxins in stool were for many years the mainstay of diagnosis, used by more than 90% of laboratories in the US [2]. When compared to TC, however, these assays showed limited sensitivity [52-75% [28, 29]]; consistent with this finding, the analytical LODs for some of the highest-performing EIAs [29] range from 0.8-2.5 ng/mL in stool [26, 27], i.e., ~1 ng/mL. Ryder et al [31] have described a cell-based assay for quantification of toxin in stool and calculated stool toxin concentrations down to as low as 30 pg/mL. Their data indicated that almost half of the toxin-positive specimens would not be detected by EIA with LODs of ~1 ng/mL. However, EIAs have been shown to have high specificity vs TC (96-98%; [28, 29]), and high clinical specificity [46, 47].

Cell culture cytotoxicity assay for direct detection of toxin in stool is re-emerging as a reference assay favored over TC. Cytotoxicity assays can have analytical LODs far below that of EIA (e.g. 1.5 pg/mL for toxin B in buffer [25]), but are complex and lengthy, making them unsuitable for routine diagnostic use. Moreover, in contrast to its low LOD in buffer, it was observed that the assay appeared to be variably sensitive for detection of toxin B in stool (see FIG. 2). One large comparison study found cytotoxicity assay to be approximately 86% sensitive compared to TC [29], and the question has been raised as to whether this difference is due to lower sensitivity of the cytotoxicity assay or the detection, by TC, of *C. difficile* organisms in the absence of toxin production [15]. Cytotoxicity assay primarily detects toxin B, which is far more potent than toxin A in this assay [48].

Given the limitations of existing toxin detection assays, over the past few years the field has made a dramatic shift towards clinical diagnosis by NAAT for the tcdA and tcdB genes, with its potential for high sensitivity and rapid turn-around time (despite higher expense). Frustratingly, despite relatively high analytical sensitivity and specificity (90-95%/94-96%, respectively, vs TC [49-51]), NAAT testing is confounded by its inability to distinguish disease from colonization or even transient contamination with environmental spores [15]. Positive predictive values for the commercial NAATs (even vs TC) are low (71-79% for prevalence <20% [51, 52]), in contrast to their high negative predictive values (98-99% in the same studies). The problem remains that like TC, NAAT indicates the presence of *C. difficile* organisms capable of producing toxin—not whether they are actually producing it (nor at what levels) in vivo [18, 48, 53, 54].

Until now, no highly sensitive assay existed that could rapidly detect and quantify both toxins A and B in stool samples at the time of diagnosis. The assays described herein have high analytical sensitivity and specificity, and given that we are detecting toxin directly, high clinical specificity—cumulative advantages that arguably may provide higher diagnostic, and even prognostic, accuracy over existing assays. As expected, the analytical sensitivity (~1 pg/mL, determined using NAAT-negative samples with uniformly low background) of the assays described herein was lower than our final clinical cutoffs (~20 pg/mL, determined using a large number of NAAT-negative samples with varied background, i.e. more representative of "real-life" sample quality). With the calculated clinical cutoff described herein, the toxin B assay has 100% sensitivity vs cytotoxicity assay, 97% specificity vs TC, and 98% specificity in samples negative by NAAT, TC, and cytotoxicity assay. As expected, 22-25% of NAAT+ and TC+ samples were negative for toxin B by the ultrasensitive digital ELISA described herein, suggesting that these sample contained toxigenic organism, but minimal or no toxin.

A final advantage of the assays described herein over existing tools is the ability to separately detect and quantify both toxins A and B. While each of the two toxins has been shown to be independently capable of causing disease, the relative contributions of the two toxin proteins to disease remains unclear (e.g. [9, 10, 55, 56]). The results provided herein suggest that patients with higher stool toxin levels are more likely to have severe CDI outcomes.

In conclusion, an ultrasensitive and quantitative digital ELISAs for *C. difficile* toxins A and B has successfully developed. These assays detect native toxins A and B in stool with analytical LODs that are ~1000-fold more sensitive than current EIAs, can quantify toxin across a 4-log range, and detect toxins from all major clinical strains tested. These assays represent the first application of Simoa to measurement of toxin A and/or toxin B of *C. difficile* in stool specimens. Many complex and important questions remain regarding these toxins and the overall pathogenesis of CDI, and the instant assays provide a new tool with which to address these questions. Moreover, the assays described herein offer the potential for a future paradigm shift in how *C. difficile* disease is diagnosed and managed.

REFERENCES

1. Freeman, J., et al., *The changing epidemiology of Clostridium difficile infections*. Clin Microbiol Rev, 2010. 23(3): p. 529-49.
2. Cohen, S. H., et al., *Clinical practice guidelines for Clostridium difficile infection in adults: 2010 update by the society for healthcare epidemiology of America (SHEA) and the infectious diseases society of America (IDSA)*. Infect Control Hosp Epidemiol, 2010. 31(5): p. 431-55.
3. Rupnik, M., M. H. Wilcox, and D. N. Gerding, *Clostridium difficile infection: new developments in epidemiology and pathogenesis*. Nat Rev Microbiol, 2009. 7(7): p. 526-36.
4. Schutze, G. E. and R. E. Willoughby, *Clostridium difficile infection in infants and children*. Pediatrics, 2013. 131(1): p. 196-200.
5. Magill, S. S., et al., *Multistate point-prevalence survey of health care-associated infections*. N Engl J Med, 2014. 370(13): p. 1198-208.
6. Kamboj, M., et al., *Relapse versus reinfection: surveillance of Clostridium difficile infection*. Clin Infect Dis, 2011. 53(10): p. 1003-6.
7. McDonald, L. C., et al., *An epidemic, toxin gene-variant strain of Clostridium difficile*. N Engl J Med, 2005. 353(23): p. 2433-41.
8. Loo, V. G., et al., *A predominantly clonal multi-institutional outbreak of Clostridium difficile-associated diarrhea with high morbidity and mortality*. N Engl J Med, 2005. 353(23): p. 2442-9.
9. Lyras, D., et al., *Toxin B is essential for virulence of Clostridium difficile*. Nature, 2009. 458(7242): p. 1176-9.
10. Kuehne, S. A., et al., *The role of toxin A and toxin B in Clostridium difficile infection*. Nature, 2010. 467(7316): p. 711-3.
11. Tenover, F. C., et al., *Laboratory diagnosis of Clostridium difficile infection can molecular amplification methods move us out of uncertainty?* J Mol Diagn, 2011. 13(6): p. 573-82.
12. Johnson, S., et al., *Fatal pseudomembranous colitis associated with a variant Clostridium Difficile strain not detected by toxin A immunoassay*. Ann Intern Med, 2001. 135(6): p. 434-8.
13. Limaye, A. P., et al., *Pseudomembranous colitis caused by a toxin A(−) B(+) strain of Clostridium difficile*. J Clin Microbiol, 2000. 38(4): p. 1696-7.
14. Antunes, A. and B. Dupuy, *Molecular methods to study transcriptional regulation of Clostridium difficile toxin genes*. Methods Mol Biol, 2010. 646: p. 93-115.
15. Wilcox, M. H., et al., *What is the current role of algorithmic approaches for diagnosis of Clostridium difficile infection?* J Clin Microbiol, 2010. 48(12): p. 4347-53.
16. Planche, T. D., et al., *Differences in outcome according to Clostridium difficile testing method: a prospective multicentre diagnostic validation study of C difficile infection*. Lancet Infect Dis, 2013. 13(11): p. 936-45.
17. Ota, K. V. and K. L. McGowan, *Clostridium difficile testing algorithms using glutamate dehydrogenase antigen and C. difficile toxin enzyme immunoassays with C. difficile nucleic acid amplification testing increase diagnostic yield in a tertiary pediatric population*. J Clin Microbiol, 2012. 50(4): p. 1185-8.
18. Selvaraju, S. B., et al., *Detection of toxigenic Clostridium difficile in pediatric stool samples: an evaluation of Quik Check Complete Antigen assay, BD GeneOhm Cdiff PCR, and ProGastro Cd PCR assays*. Diagn Microbiol Infect Dis, 2011. 71(3): p. 224-9.
19. Koo, H. L., et al., *Real-Time Polymerase Chain Reaction Detection of Asymptomatic Clostridium difficile Colonization and Rising C. difficile-Associated Disease Rates*. Infect Control Hosp Epidemiol, 2014. 35(6): p. 667-73.
20. Leibowitz, J., et al., *Similar Proportions of Stool Specimens from Hospitalized Children with and without Diarrhea Test Positive for Clostridium difficile*. Pediatr Infect Dis J, 2014.
21. McFarland, L. V., et al., *Nosocomial acquisition of Clostridium difficile infection*. N Engl J Med, 1989. 320 (4): p. 204-10.
22. Kelly, C. P. and J. T. LaMont, *Clostridium difficile—more difficult than ever*. N Engl J Med, 2008. 359(18): p. 1932-40.
23. McFarland, L. V., S. A. Brandmarker, and S. Guandalini, *Pediatric Clostridium difficile: a phantom menace or clinical reality?* J Pediatr Gastroenterol Nutr, 2000. 31(3): p. 220-31.
24. Karlsson, S., L. G. Burman, and T. Akerlund, *Induction of toxins in Clostridium difficile is associated with dramatic changes of its metabolism*. Microbiology, 2008. 154(Pt 11): p. 3430-6.
25. Kelly, C. P., et al., *Anti-Clostridium difficile bovine immunoglobulin concentrate inhibits cytotoxicity and enterotoxicity of C. difficile toxins*. Antimicrob Agents Chemother, 1996. 40(2): p. 373-9.
26. *Premier Toxins A & B Package Insert, Meridian Bioscience, Inc. Rev.* April 2009.
27. *C. difficile Tox A/B II Package Insert, TechLab, Inc. Issued* March 2008.
28. Crobach, M. J., et al., *European Society of Clinical Microbiology and Infectious Diseases (ESCMID): data review and recommendations for diagnosing Clostridium difficile-infection (CDI)*. Clin Microbiol Infect, 2009. 15(12): p. 1053-66.
29. Eastwood, K., et al., *Comparison of nine commercially available Clostridium difficile toxin detection assays, a real-time PCR assay for C. difficile tcdB, and a glutamate* dehydrogenase detection assay to cytotoxin testing and cytotoxigenic culture methods. J Clin Microbiol, 2009. 47(10): p. 3211-7.
30. Akerlund, T., et al., *Correlation of disease severity with fecal toxin levels in patients with Clostridium difficile-associated diarrhea and distribution of PCR ribotypes and toxin yields in vitro of corresponding isolates*. J Clin Microbiol, 2006. 44(2): p. 353-8.
31. Ryder, A. B., et al., *Assessment of Clostridium difficile infections by quantitative detection of tcdB toxin by use of a real-time cell analysis system*. J Clin Microbiol, 2010. 48(11): p. 4129-34.
32. Rissin, D. M., et al., *Single-molecule enzyme-linked immunosorbent assay detects serum proteins at subfemtomolar concentrations*. Nat Biotechnol, 2010. 28(6): p. 595-9.
33. Rissin, D. M., et al., *Simultaneous detection of single molecules and singulated ensembles of molecules enables immunoassays with broad dynamic range*. Anal Chem, 2011. 83(6): p. 2279-85.
34. Wilson, D. H., et al., *Fifth-generation digital immunoassay for prostate-specific antigen by single molecule array technology*. Clin Chem, 2011. 57(12): p. 1712-21.
35. Lepor, H., et al., *Clinical evaluation of a novel method for the measurement of prostate-specific antigen, AccuPSA™, as a predictor of 5-year biochemical recurrence free survival after radical prostatectomy: results of a pilot study*. BJU Int, 2011.
36. Song, L., et al., *Single molecule measurements of tumor necrosis factor alpha and interleukin-6 in the plasma of patients with Crohn's disease*. J Immunol Methods, 2011. 372(1-2): p. 177-86.
37. Zetterberg, H., et al., *Hypoxia Due to Cardiac Arrest Induces a Time-Dependent Increase in Serum Amyloid beta Levels in Humans*. PLoS One, 2011. 6(12): p. e28263.
38. Kyne, L., et al., *Asymptomatic carriage of Clostridium difficile and serum levels of IgG antibody against toxin A*. N Engl J Med, 2000. 342(6): p. 390-7.
39. Kan, C. W., et al., *Isolation and detection of single molecules on paramagnetic beads using sequential fluid flows in microfabricated polymer array assemblies*. Lab Chip, 2012. 12(5): p. 977-85.
40. Tenover, F. C., et al., *Comparison of strain typing results for Clostridium difficile isolates from North America*. J Clin Microbiol, 2011. 49(5): p. 1831-7.
41. Clabots, C. R., et al., *Development of a rapid and efficient restriction endonuclease analysis typing system for Clostridium difficile and correlation with other typing systems*. J Clin Microbiol, 1993. 31(7): p. 1870-5.
42. Petrella, L. A., et al., *Decreased cure and increased recurrence rates for Clostridium difficile infection caused by the epidemic C. difficile BI strain*. Clin Infect Dis, 2012. 55(3): p. 351-7.
43. *VIDAS C. difficile Toxin A & B package insert, BioMerieux*, May 2011.
44. *Meridian ImmunoCard Toxins A & B*, April 2009.
45. Cloud, J., et al., *Clostridium difficile strain NAP-1 is not associated with severe disease in a nonepidemic setting*. Clin Gastroenterol Hepatol, 2009. 7(8): p. 868-873 e2.
46. Polage, C. R., et al., *Outcomes in patients tested for Clostridium difficile toxins*. Diagn Microbiol Infect Dis, 2012. 74(4): p. 369-73.
47. Baker, I., et al., *Clinical relevance of a positive molecular test in the diagnosis of Clostridium difficile infection*. J Hosp Infect, 2013. 84(4): p. 311-5.
48. He, X., et al., *An ultrasensitive rapid immunocytotoxicity assay for detecting Clostridium difficile toxins*. J Microbiol Methods, 2009. 78(1): p. 97-100.
49. GeneXpert *C. difficile package insert, Cepheid, Inc.* Revised May 2012.
50. *Illumigene C. difficile package insert, Meridian Bioscience, Inc.* Revised February 2011.
51. Deshpande, A., et al., *Diagnostic accuracy of real-time polymerase chain reaction in detection of Clostridium difficile in the stool samples of patients with suspected Clostridium difficile Infection: a meta-analysis*. Clin Infect Dis, 2011. 53(7): p. e81-90.
52. Tenover, F. C., et al., *Impact of strain type on detection of toxigenic Clostridium difficile: comparison of molecular diagnostic and enzyme immunoassay approaches*. J Clin Microbiol, 2010. 48(10): p. 3719-24.
53. Rousseau, C., et al., *Prevalence and diversity of Clostridium difficile strains in infants*. J Med Microbiol, 2011. 60(Pt 8): p. 1112-8.
54. Kawsar, H. I., *Effective utilization of evolving methods for the laboratory diagnosis of Clostridium difficile infection*. Clin Infect Dis, 2011. 53(9): p. 964; author's reply 964-5.
55. Kader, H. A., et al., *Single toxin detection is inadequate to diagnose Clostridium difficile diarrhea in pediatric patients*. Gastroenterology, 1998. 115(6): p. 1329-34.
56. Riegler, M., et al., *Clostridium difficile toxin B is more potent than toxin A in damaging human colonic epithelium in vitro*. J Clin Invest, 1995. 95(5): p. 2004-11.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for measuring a level of multiple toxins of *Clostridium difficile* (*C. difficile*) in a stool sample suspected of containing a *C. difficile* strain and/or a toxin thereof, comprising:
   (i) providing the stool sample suspected of containing a *C. difficile* strain and/or a toxin thereof,
   (ii) measuring a level of toxin B of the *C. difficile* in the stool sample using an optical interrogation-based ELISA having a limit of detection of no greater than 20 pg/mL for toxin B in stool, and
   (iii) measuring a level of toxin A of the *C. difficile* in the stool sample using an optical interrogation-based ELISA having a limit of detection of no greater than 10 pg/mL for toxin A in stool.

2. A method for treating *Clostridium difficile* (*C. difficile*) infection in a subject, comprising: selecting a subject having a diagnosis of *C. difficile* infection, the diagnosis a made by a method comprising:
   (i) determining that the subject manifests a symptom associated with *C. difficile* infection; and (ii) determining a level of toxin A, toxin B, or both in a stool sample obtained from the subject, using an optical interrogation-based assay having a limit of detection of about:
   (a) no greater than 10 pg/mL for toxin A in stool, and
   (b) no greater than 20 pg/mL for toxin B in stool; and
   administering a suitable anti-*C. difficile* drug to the subject.

3. The method of claim 2, wherein step (ii) is performed at a level of detection of about:
   (a) 0.3 to 10 pg/mL for toxin A in stool, and
   (b) 1 to 20 pg/mL for toxin B in stool.

4. The method of claim 3, wherein the level of toxin B determined being higher than 20 pg/ml indicates that the subject has *C. difficile* infection.

5. The method of claim 3, wherein the symptom is diarrhea.

6. The method of claim 3, wherein step (ii) is performed by a differential detection method to determine whether the sample contains a highly virulent strain or a less virulent strain.

7. The method of claim 1, wherein the stool sample is processed via dilution and filtration prior to step (ii) and step (iii).

8. The method of claim 3, wherein the method on which the diagnosis is based further comprises detecting the presence of a nucleic acid that encodes toxin A, a nucleic acid that encodes toxin B, or both, in a sample obtained from the subject.

9. The method of claim 3, wherein the stool sample is processed via dilution and filtration prior to step (ii).

10. The method of claim 3, wherein step (ii) is performed at a level of detection of about 10 pg/mL for toxin A in stool.

11. The method of claim 3, wherein step (ii) is performed at a level of detection of about 5 pg/mL for toxin A in stool.

12. The method of claim 3, wherein step (ii) is performed at a level of detection of about 1 pg/mL for toxin A in stool.

13. The method of claim 3, wherein step (ii) is performed at a level of detection of about 0.45 pg/mL for toxin A in stool.

14. The method of claim 3, wherein step (ii) is performed at a level of detection of about 0.3 pg/mL for toxin A in stool.

15. The method of claim 3, wherein step (ii) is performed at a level of detection of about 20 pg/mL for toxin B in stool.

16. The method of claim 3, wherein step (ii) is performed at a level of detection of about 15 pg/mL for toxin B in stool.

17. The method of claim 3, wherein step (ii) is performed at a level of detection of about 5 pg/mL for toxin B in stool.

18. The method of claim 3, wherein step (ii) is performed at a level of detection of about 1.5 pg/mL for toxin B in stool.

19. The method of claim 3, wherein step (ii) is performed at a level of detection of about 1 pg/mL for toxin B in stool.

20. The method of claim 3, wherein step (ii) is not performed using a cytotoxicity assay.

21. The method of claim 1, wherein:
    (a) step (ii) is performed at a limit of detection of about 1 to 20 pg/mL for toxin B in stool, and
    (b) step (iii) is performed at a limit of detection of about 0.3 to 10 pg/mL for toxin A in stool.

22. The method of claim 21, wherein step (ii) and step (iii) each comprises detecting a fluorescence signal.

23. The method of claim 3, wherein step (ii) comprises detecting a fluorescence signal.

24. The method of claim 21, wherein the measuring a level of toxin B of the *C. difficile* in the stool sample using an optical interrogation-based ELISA comprises:
    (a) exposing a plurality of capture objects that each include a binding surface having affinity for toxin B molecules to the stool sample;
    (b) associating at least some of the toxin B molecules from the stool sample with respect to the plurality of capture objects such that at least some of the capture objects associate with at least one toxin B molecule and a statistically significant fraction of the capture objects do not associate with any toxin B molecules;
    (c) determining, via optical interrogation, a measure indicative of a number of the plurality of capture objects that associated with a toxin B molecule in step (b); and
    (d) determining a level of toxin B in the stool sample based at least in part on the measure indicative of a number determined in step (c).

25. The method of claim 21, wherein the determining a level of toxin A of the *C. difficile* in the stool sample using an optical interrogation-based ELISA comprises:
    (a) exposing a plurality of capture objects that each include a binding surface having affinity for toxin A molecules to the stool sample;
    (b) associating at least some of the toxin A molecules from the stool sample with respect to the plurality of capture objects such that at least some of the capture objects associate with at least one toxin A molecule and a statistically significant fraction of the capture objects do not associate with any toxin A molecules;
    (c) determining, via optical interrogation, a measure indicative of a number of the plurality of capture objects that associated with a toxin A molecule in step (b); and
    (d) determining a level of toxin A in the stool sample based at least in part on the measure indicative of a number determined in step (c).

26. The method of claim 3, wherein step (ii) comprises
    (a) exposing a plurality of capture objects that each include a binding surface having affinity for toxin A molecules and/or toxin B molecules to the stool sample;
    (b) associating at least some of the toxin A molecules and/or toxin B molecules from the stool sample with respect to the plurality of capture objects such that at least some of the capture objects associate with at least one toxin A molecule and/or toxin B molecule and a statistically significant fraction of the capture objects do not associate with any toxin A molecules or toxin B molecules;
    (c) determining, via optical interrogation, a measure indicative of a number of the plurality of capture objects that associated with a toxin A molecule and/or a toxin B molecule in step (b); and
    (d) determining a level of toxin A and/or a level of toxin B in the stool sample based at least in part on the measure indicative of a number determined in step (c).

27. The method of claim 3, wherein the anti-*C. difficile* drug is an antibiotic drug.

28. The method of claim 27, wherein the antibiotic drug comprises metronidazole, fidaxomicin, and/or vancomycin.

29. A method for treating *Clostridium difficile* (*C. difficile*) infection in a subject, comprising:
    (i) determining that the subject manifests a symptom associated with *C. difficile* infection;
    (ii) determining a level of toxin A, toxin B, or both in a stool sample obtained from the subject, using an optical interrogation-based assay having a limit of detection of about:
        (a) no greater than 10 pg/mL for toxin A in stool, and
        (b) no greater than 20 pg/mL for toxin B in stool;
    (iii) determining based on the results of step (ii) that the subject has *C. difficile* infection; and
    (iv) administering a suitable anti-*C. difficile* drug to the subject.

30. A method for treating *Clostridium difficile* (*C. difficile*) infection in a subject, comprising:
    administering a suitable anti-*C. difficile* drug to a subject diagnosed with *C. difficile* infection, the diagnosis having been made based on a method comprising:
        (i) determining that the subject manifests a symptom associated with *C. difficile* infection; and
        (ii) determining a level of toxin A, toxin B, or both in a stool sample obtained from the subject, using an optical interrogation-based assay having a limit of detection of about:
            (a) no greater than 10 pg/mL for toxin A in stool, and
            (b) no greater than 20 pg/mL for toxin B in stool.

* * * * *